(12) United States Patent
Gray et al.

(10) Patent No.: US 9,173,996 B2
(45) Date of Patent: *Nov. 3, 2015

(54) INFUSION SET FOR A FLUID PUMP

(75) Inventors: Larry B. Gray, Merrimack, NH (US);
Jared Hamilton, Manchester, NH (US);
Richard Lanigan, Concord, NH (US);
Brian Tracey, Litchfield, NH (US)

(73) Assignee: DEKA Products Limited Partnership, Manchester, NH (US)

(*) Notice: Subject to any disclaimer, the term of this patent is extended or adjusted under 35 U.S.C. 154(b) by 2028 days.

This patent is subject to a terminal disclaimer.

(21) Appl. No.: 11/533,882
(22) Filed: Sep. 21, 2006

(65) Prior Publication Data

US 2007/0049870 A1 Mar. 1, 2007

Related U.S. Application Data

(63) Continuation of application No. 10/151,733, filed on May 20, 2002, now abandoned, which is a continuation-in-part of application No. 10/037,614, filed on Jan. 4, 2002, now Pat. No. 7,306,578.

(60) Provisional application No. 60/291,881, filed on May 18, 2001.

(51) Int. Cl.
*A61M 5/178* (2006.01)
*A61M 5/145* (2006.01)
(Continued)

(52) U.S. Cl.
CPC .............. *A61M 5/1456* (2013.01); *A61M 5/158* (2013.01); *A61M 5/14* (2013.01); *A61M 5/142* (2013.01);
(Continued)

(58) Field of Classification Search
CPC ..... A61M 5/14; A61M 5/142; A61M 5/1452; A61M 5/1456; A61M 5/158; A61M 39/14; A61M 39/1011; A61M 25/0612; A61M 2005/14573; A61M 2005/1581; A61M 2005/1587
USPC ...................... 604/65–67, 131, 151–155, 183, 604/533–535
See application file for complete search history.

(56) References Cited

U.S. PATENT DOCUMENTS 3,631,847 A 1/1972 Hobbs, II
3,692,027 A 9/1972 Ellinwood, Jr.
(Continued)

FOREIGN PATENT DOCUMENTS

DE 4329229 A1 3/1995
DE 19627619 A1 1/1998
(Continued)

OTHER PUBLICATIONS

Japanese Office Action, Jun. 10, 2008, received in Japanese patent application No. 2002-591,067, 4 pgs.
(Continued)

*Primary Examiner* — Matthew F Desanto
(74) *Attorney, Agent, or Firm* — McCormick, Paulding & Huber LLP

(57) ABSTRACT

A medical device for delivery of a fluid to a patient from a line terminating in a tubing needle. The medical device includes a cannula assembly for coupling the fluid into a cannula that is inserted into the patient. The cannula assembly has a first locking element disposed in a fixed position with respect to the cannula. Coupling the line to the cannula assembly is an infusion flap. The infusion flap includes a second locking element for engaging the first locking element of the cannula assembly and a lift tab for disconnecting the infusion flap from the cannula assembly. Coupling of the first and second locking elements requires initial mating of the infusion flap and cannula assembly followed by locking through rotation of the infusion flap with respect to the cannula assembly.

10 Claims, 27 Drawing Sheets

(51) Int. Cl.
  *A61M 5/158* (2006.01)
  *A61M 5/14* (2006.01)
  *A61M 5/142* (2006.01)
  *A61M 25/06* (2006.01)
  *A61M 39/10* (2006.01)
  *A61M 39/14* (2006.01)

(52) U.S. Cl.
  CPC .......... *A61M 5/1452* (2013.01); *A61M 25/0612* (2013.01); *A61M 39/1011* (2013.01); *A61M 39/14* (2013.01); *A61M 2005/14573* (2013.01); *A61M 2005/1581* (2013.01); *A61M 2005/1587* (2013.01)

(56) References Cited

U.S. PATENT DOCUMENTS

| | | |
|---|---|---|
| 3,752,510 A | 8/1973 | Windischman et al. |
| 3,811,121 A | 5/1974 | Heim et al. |
| 3,811,122 A | 5/1974 | Raber et al. |
| 3,837,339 A | 9/1974 | Aisenberg et al. |
| 3,887,393 A | 6/1975 | La Rue, Jr. |
| 3,951,147 A | 4/1976 | Tucker et al. |
| D248,873 S | 8/1978 | Raitto |
| 4,123,631 A | 10/1978 | Lewis |
| 4,146,029 A | 3/1979 | Ellinwood, Jr. |
| 4,150,672 A | 4/1979 | Martin |
| D254,446 S | 3/1980 | Raitto |
| 4,206,274 A | 6/1980 | Peels |
| 4,215,701 A | 8/1980 | Raitto |
| 4,267,836 A | 5/1981 | Whitney et al. |
| 4,269,908 A | 5/1981 | Stemme |
| 4,270,532 A | 6/1981 | Franetzki et al. |
| 4,273,121 A | 6/1981 | Jassawalla |
| 4,282,872 A | 8/1981 | Franetzki et al. |
| 4,296,949 A | 10/1981 | Muetterties et al. |
| 4,331,262 A | 5/1982 | Snyder et al. |
| 4,371,594 A | 2/1983 | Ohara et al. |
| 4,373,527 A | 2/1983 | Fischell |
| 4,391,883 A | 7/1983 | Williamson et al. |
| 4,392,847 A | 7/1983 | Whitney et al. ............... 604/118 |
| 4,392,849 A | 7/1983 | Petre et al. |
| 4,395,259 A | 7/1983 | Prestele et al. |
| 4,437,859 A | 3/1984 | Whitehouse et al. |
| 4,443,218 A | 4/1984 | DeCant, Jr. et al. |
| 4,464,170 A | 8/1984 | Clemens et al. |
| 4,469,481 A | 9/1984 | Kobayashi |
| 4,475,901 A | 10/1984 | Kraegen et al. |
| 4,493,704 A | 1/1985 | Beard et al. ................... 604/154 |
| 4,494,950 A | 1/1985 | Fischell |
| 4,498,843 A | 2/1985 | Schneider et al. |
| 4,533,346 A | 8/1985 | Cosgrove, Jr. et al. |
| 4,542,532 A | 9/1985 | McQuilkin |
| 4,543,093 A | 9/1985 | Christinger |
| 4,550,731 A | 11/1985 | Batina et al. |
| 4,559,037 A | 12/1985 | Franetzki et al. |
| 4,559,038 A | 12/1985 | Berg et al. |
| 4,561,856 A | 12/1985 | Cochran |
| 4,562,751 A | 1/1986 | Nason et al. |
| 4,596,575 A | 6/1986 | Rosenberg et al. |
| 4,624,661 A | 11/1986 | Arimond |
| 4,633,878 A | 1/1987 | Bombardieri |
| 4,648,872 A | 3/1987 | Kamen .......................... 604/155 |
| 4,673,396 A | 6/1987 | Urbaniak |
| 4,678,408 A | 7/1987 | Nason et al. |
| 4,685,903 A | 8/1987 | Cable et al. |
| 4,690,878 A | 9/1987 | Nakamura |
| 4,693,684 A | 9/1987 | Blatherwick et al. |
| 4,696,671 A | 9/1987 | Epstein et al. |
| 4,714,463 A | 12/1987 | Archibald et al. |
| 4,731,051 A | 3/1988 | Fischell |
| 4,731,726 A | 3/1988 | Allen, III |
| 4,735,441 A | 4/1988 | Stephens |
| 4,741,731 A | 5/1988 | Starck et al. |
| 4,743,895 A | 5/1988 | Alexander |
| 4,747,828 A | 5/1988 | Tseo |
| 4,790,028 A | 12/1988 | Ramage |
| 4,803,625 A | 2/1989 | Fu et al. |
| 4,804,368 A | 2/1989 | Skakoon et al. |
| 4,809,697 A | 3/1989 | Causey, III et al. |
| 4,826,810 A | 5/1989 | Aoki |
| 4,834,712 A | 5/1989 | Quinn et al. ................... 604/175 |
| 4,849,852 A | 7/1989 | Mullins |
| 4,856,340 A | 8/1989 | Garrison |
| 4,871,351 A | 10/1989 | Feingold |
| 4,880,712 A | 11/1989 | Gordecki |
| 4,881,063 A | 11/1989 | Fawcett |
| 4,898,578 A | 2/1990 | Rubalcaba, Jr. |
| 4,919,650 A | 4/1990 | Feingold et al. |
| 4,954,000 A | 9/1990 | Gueret |
| 4,959,640 A | 9/1990 | Hall |
| 4,972,508 A | 11/1990 | King |
| 4,988,337 A | 1/1991 | Ito |
| 4,997,423 A | 3/1991 | Okuda et al. |
| 5,009,646 A | 4/1991 | Sudo et al. |
| 5,019,974 A | 5/1991 | Beckers |
| 5,034,004 A | 7/1991 | Crankshaw |
| 5,049,141 A | 9/1991 | Olive |
| 5,050,612 A | 9/1991 | Matsumura |
| 5,055,830 A | 10/1991 | Cousins et al. |
| 5,063,291 A | 11/1991 | Buehring |
| 5,078,683 A | 1/1992 | Sancoff et al. |
| 5,080,653 A | 1/1992 | Voss et al. |
| 5,088,981 A | 2/1992 | Howson et al. |
| 5,101,814 A | 4/1992 | Palti |
| 5,102,388 A | 4/1992 | Richmond |
| 5,103,216 A | 4/1992 | Sisselman |
| 5,104,374 A | 4/1992 | Bishko et al. |
| 5,150,314 A | 9/1992 | Garratt et al. |
| 5,153,827 A | 10/1992 | Coutré et al. |
| 5,165,407 A | 11/1992 | Wilson et al. |
| 5,174,716 A | 12/1992 | Hora et al. |
| 5,176,502 A | 1/1993 | Sanderson et al. |
| 5,176,644 A | 1/1993 | Srisathapat et al. |
| 5,176,662 A | 1/1993 | Bartholomew et al. |
| 5,181,910 A | 1/1993 | Scanlon |
| 5,187,746 A | 2/1993 | Narisawa |
| 5,191,855 A | 3/1993 | Conforti |
| 5,197,322 A | 3/1993 | Indravudh |
| 5,197,895 A | 3/1993 | Stupecky |
| 5,205,819 A | 4/1993 | Ross et al. |
| 5,216,597 A | 6/1993 | Beckers |
| 5,217,442 A | 6/1993 | Davis |
| 5,248,569 A | 9/1993 | Pine et al. |
| 5,254,093 A | 10/1993 | Bartlett et al. |
| 5,254,096 A | 10/1993 | Rondelet et al. |
| 5,257,971 A | 11/1993 | Lord et al. |
| 5,257,980 A | 11/1993 | Van Antwerp et al. |
| 5,270,702 A | 12/1993 | Krolak |
| 5,290,639 A | 3/1994 | Mallory |
| 5,304,152 A | 4/1994 | Sams |
| 5,307,263 A | 4/1994 | Brown |
| 5,314,416 A | 5/1994 | Lewis et al. |
| 5,317,506 A | 5/1994 | Coutré et al. |
| 5,337,215 A | 8/1994 | Sunderland et al. |
| 5,338,157 A | 8/1994 | Blomquist |
| 5,339,821 A | 8/1994 | Fujimoto |
| 5,341,291 A | 8/1994 | Roizen et al. |
| 5,342,324 A | 8/1994 | Tucker .......................... 604/264 |
| 5,349,852 A | 9/1994 | Kamen et al. |
| 5,350,411 A | 9/1994 | Ryan et al. |
| 5,357,427 A | 10/1994 | Langen et al. |
| 5,364,242 A | 11/1994 | Olsen |
| 5,364,346 A | 11/1994 | Schrezenmeir |
| 5,368,562 A | 11/1994 | Blomquist et al. |
| 5,370,622 A | 12/1994 | Livingston et al. |
| 5,372,133 A | 12/1994 | Hogen Esch |
| 5,376,070 A | 12/1994 | Purvis et al. |
| 5,383,865 A | 1/1995 | Michel |
| 5,389,078 A | 2/1995 | Zalesky et al. |
| 5,390,671 A | 2/1995 | Lord et al. |
| 5,391,157 A | 2/1995 | Harris et al. |
| 5,399,823 A | 3/1995 | McCusker |
| 5,403,648 A | 4/1995 | Chan et al. |

(56) References Cited

U.S. PATENT DOCUMENTS

| | | | | |
|---|---|---|---|---|
| 5,405,614 | A | 4/1995 | D'Angelo et al. | |
| 5,417,667 | A | 5/1995 | Tennican et al. | 604/191 |
| 5,429,602 | A | 7/1995 | Hauser | |
| 5,433,710 | A | 7/1995 | VanAntwerp et al. | |
| 5,450,003 | A | 9/1995 | Cheon | |
| 5,456,940 | A | 10/1995 | Funderburk | |
| 5,460,618 | A | 10/1995 | Harreld | |
| 5,462,525 | A | 10/1995 | Srisathapat et al. | |
| 5,464,392 | A | 11/1995 | Epstein et al. | |
| 5,466,218 | A | 11/1995 | Srisathapat et al. | |
| 5,472,317 | A | 12/1995 | Field et al. | |
| 5,476,460 | A | 12/1995 | Montalvo | |
| 5,478,211 | A | 12/1995 | Dominiak et al. | |
| 5,482,446 | A | 1/1996 | Williamson et al. | |
| 5,497,772 | A | 3/1996 | Schulman et al. | |
| 5,505,709 | A | 4/1996 | Funderburk et al. | |
| 5,507,727 | A | 4/1996 | Crainich | 604/97 |
| 5,508,690 | A | 4/1996 | Shur et al. | |
| 5,514,097 | A | 5/1996 | Knauer | |
| 5,514,103 | A | 5/1996 | Srisathapat et al. | |
| 5,522,803 | A | 6/1996 | Teissen-Simony | 604/177 |
| 5,526,844 | A | 6/1996 | Kamen et al. | |
| 5,527,307 | A | 6/1996 | Srisathapat et al. | |
| 5,528,359 | A | 6/1996 | Taguchi | |
| 5,531,697 | A | 7/1996 | Olsen et al. | |
| 5,531,698 | A | 7/1996 | Olsen | |
| 5,533,389 | A | 7/1996 | Kamen et al. | |
| 5,533,996 | A | 7/1996 | Murphey et al. | 604/283 |
| 5,538,399 | A | 7/1996 | Johnson | |
| 5,540,564 | A | 7/1996 | Klopfer | |
| 5,543,588 | A | 8/1996 | Bisset et al. | |
| 5,545,140 | A | 8/1996 | Conero et al. | |
| 5,545,142 | A | 8/1996 | Stephens et al. | |
| 5,545,143 | A | 8/1996 | Fischell | 604/180 |
| 5,545,152 | A | 8/1996 | Funderburk et al. | 604/283 |
| 5,558,640 | A | 9/1996 | Pfeiler et al. | |
| 5,558,641 | A | 9/1996 | Glantz et al. | 604/93 |
| 5,562,618 | A | 10/1996 | Cai et al. | 604/93 |
| 5,564,915 | A | 10/1996 | Johnson | |
| 5,567,119 | A | 10/1996 | Johnson | |
| 5,567,136 | A | 10/1996 | Johnson | |
| 5,569,026 | A | 10/1996 | Novak | 417/477.1 |
| 5,569,186 | A | 10/1996 | Lord et al. | |
| 5,569,187 | A | 10/1996 | Kaiser | |
| 5,573,506 | A | 11/1996 | Vasko | |
| 5,575,310 | A | 11/1996 | Kamen et al. | |
| 5,582,593 | A | 12/1996 | Hultman | |
| 5,584,813 | A | 12/1996 | Livingston et al. | 604/177 |
| 5,593,390 | A | 1/1997 | Castellano et al. | |
| 5,594,638 | A | 1/1997 | Iliff | |
| 5,609,060 | A | 3/1997 | Dent | |
| 5,609,575 | A | 3/1997 | Larson et al. | |
| 5,613,945 | A | 3/1997 | Cai et al. | |
| 5,620,312 | A | 4/1997 | Hyman et al. | |
| 5,626,144 | A | 5/1997 | Tacklind et al. | |
| 5,630,710 | A | 5/1997 | Tune et al. | |
| 5,632,729 | A | 5/1997 | Cai et al. | |
| 5,637,095 | A | 6/1997 | Nason et al. | |
| 5,637,420 | A | 6/1997 | Jones, Jr. et al. | |
| 5,641,892 | A | 6/1997 | Larkins et al. | |
| 5,643,212 | A | 7/1997 | Coutré et al. | |
| 5,647,853 | A | 7/1997 | Feldmann et al. | |
| 5,647,854 | A | 7/1997 | Olsen et al. | 604/174 |
| 5,651,775 | A | 7/1997 | Walker et al. | |
| 5,658,133 | A | 8/1997 | Anderson et al. | |
| 5,658,250 | A | 8/1997 | Blomquist et al. | |
| 5,658,252 | A | 8/1997 | Johnson | |
| 5,660,176 | A | 8/1997 | Iliff | |
| 5,665,065 | A | 9/1997 | Colman et al. | |
| 5,669,877 | A | 9/1997 | Blomquist | |
| 5,669,887 | A | 9/1997 | Cooper | |
| 5,678,568 | A | 10/1997 | Uchikubo et al. | |
| 5,681,285 | A | 10/1997 | Ford et al. | |
| 5,685,844 | A | 11/1997 | Marttila | |
| 5,687,734 | A | 11/1997 | Dempsey et al. | |
| 5,695,473 | A | 12/1997 | Olsen | |
| 5,704,366 | A | 1/1998 | Tacklind et al. | |
| 5,713,856 | A | 2/1998 | Eggers et al. | |
| 5,713,857 | A | 2/1998 | Grimard et al. | |
| 5,716,725 | A | 2/1998 | Riveron et al. | |
| 5,718,562 | A | 2/1998 | Lawless et al. | |
| 5,720,729 | A | 2/1998 | Kriesel | |
| 5,727,241 | A | 3/1998 | Yamano et al. | |
| 5,733,673 | A | 3/1998 | Kunert | |
| 5,743,873 | A | 4/1998 | Cai et al. | |
| 5,752,940 | A | 5/1998 | Grimard | |
| 5,755,744 | A | 5/1998 | Shaw et al. | |
| 5,762,632 | A | 6/1998 | Whisson | 604/171 |
| 5,764,159 | A | 6/1998 | Neftel | |
| 5,772,409 | A | 6/1998 | Johnson | |
| 5,772,635 | A | 6/1998 | Dastur et al. | |
| 5,776,116 | A | 7/1998 | Lopez et al. | 604/283 |
| 5,779,665 | A | 7/1998 | Mastrototaro et al. | |
| 5,785,681 | A | 7/1998 | Indravudh | |
| 5,788,669 | A | 8/1998 | Peterson | |
| 5,788,671 | A | 8/1998 | Johnson | |
| 5,788,673 | A | 8/1998 | Young et al. | |
| 5,788,678 | A | 8/1998 | Van Antwerp | |
| 5,795,337 | A | 8/1998 | Grimard | |
| 5,800,387 | A | 9/1998 | Duffy et al. | |
| 5,800,420 | A | 9/1998 | Gross et al. | |
| 5,801,600 | A | 9/1998 | Butland et al. | |
| 5,807,336 | A | 9/1998 | Russo et al. | |
| 5,810,001 | A | 9/1998 | Genga et al. | 128/202.27 |
| 5,810,771 | A | 9/1998 | Blomquist | |
| 5,814,015 | A | 9/1998 | Gargano et al. | |
| 5,822,715 | A | 10/1998 | Worthington et al. | |
| 5,823,746 | A | 10/1998 | Johnson | |
| 5,832,448 | A | 11/1998 | Brown | |
| 5,840,020 | A | 11/1998 | Heinonen et al. | |
| 5,840,026 | A | 11/1998 | Uber, III et al. | |
| 5,843,146 | A | 12/1998 | Cross, Jr. | 607/115 |
| 5,851,197 | A | 12/1998 | Marano et al. | |
| 5,851,692 | A | 12/1998 | Potts | |
| 5,861,018 | A | 1/1999 | Feierbach | |
| 5,868,669 | A | 2/1999 | Iliff | |
| 5,871,465 | A | 2/1999 | Vasko | |
| 5,876,370 | A | 3/1999 | Blomquist | |
| 5,879,143 | A | 3/1999 | Cote et al. | |
| 5,879,144 | A | 3/1999 | Johnson | |
| 5,879,163 | A | 3/1999 | Brown et al. | |
| 5,882,256 | A | 3/1999 | Shropshire | |
| 5,885,245 | A | 3/1999 | Lynch et al. | |
| 5,897,493 | A | 4/1999 | Brown | |
| 5,899,855 | A | 5/1999 | Brown | |
| 5,913,310 | A | 6/1999 | Brown | |
| 5,918,603 | A | 7/1999 | Brown | |
| 5,925,021 | A | 7/1999 | Castellano et al. | |
| 5,928,196 | A | 7/1999 | Johnson et al. | |
| 5,928,202 | A | 7/1999 | Linnebjerg | |
| 5,931,791 | A | 8/1999 | Saltzstein et al. | |
| 5,933,136 | A | 8/1999 | Brown | |
| 5,935,099 | A | 8/1999 | Peterson et al. | |
| 5,935,105 | A | 8/1999 | Manning et al. | |
| 5,935,106 | A | 8/1999 | Olsen | |
| 5,940,801 | A | 8/1999 | Brown | |
| 5,951,521 | A | 9/1999 | Mastrototaro et al. | |
| 5,954,485 | A | 9/1999 | Johnson et al. | |
| 5,954,697 | A | 9/1999 | Srisathapat et al. | 604/155 |
| 5,954,700 | A | 9/1999 | Kovelman | |
| 5,956,501 | A | 9/1999 | Brown | |
| 5,957,890 | A | 9/1999 | Mann et al. | |
| 5,960,403 | A | 9/1999 | Brown | |
| 5,968,011 | A | 10/1999 | Larsen et al. | 604/93 |
| 5,971,963 | A | 10/1999 | Choi | |
| 5,973,623 | A | 10/1999 | Gupta et al. | |
| 5,980,506 | A | 11/1999 | Mathiasen | 604/535 |
| 5,989,216 | A | 11/1999 | Johnson et al. | |
| 5,989,227 | A | 11/1999 | Vetter et al. | |
| 5,997,476 | A | 12/1999 | Brown | |
| 6,007,941 | A | 12/1999 | Hermann et al. | |
| 6,009,339 | A | 12/1999 | Bentsen et al. | |
| 6,014,587 | A | 1/2000 | Shaw et al. | |
| 6,017,326 | A | 1/2000 | Pasqualucci et al. | 604/153 |

(56) References Cited

U.S. PATENT DOCUMENTS

| | | | |
|---|---|---|---|
| 6,017,328 A | 1/2000 | Fischell et al. ............... 604/180 |
| 6,024,539 A | 2/2000 | Blomquist |
| 6,032,119 A | 2/2000 | Brown et al. |
| 6,042,565 A | 3/2000 | Hirschman et al. .......... 604/155 |
| 6,056,522 A | 5/2000 | Johnson |
| 6,056,718 A | 5/2000 | Funderburk et al. ........... 604/93 |
| 6,059,753 A | 5/2000 | Faust et al. |
| 6,063,059 A | 5/2000 | Kriesel ........................ 604/133 |
| 6,073,036 A | 6/2000 | Heikkinen et al. |
| 6,077,055 A | 6/2000 | Vilks |
| 6,086,575 A | 7/2000 | Mejslov ........................ 604/533 |
| 6,090,071 A | 7/2000 | Kriesel |
| 6,090,081 A | 7/2000 | Sudo et al. |
| 6,093,172 A | 7/2000 | Funderburk et al. |
| 6,096,011 A | 8/2000 | Trombley, III et al. ....... 604/256 |
| 6,099,507 A | 8/2000 | Heinzerling .................. 604/174 |
| 6,101,478 A | 8/2000 | Brown |
| 6,110,152 A | 8/2000 | Kovelman |
| 6,112,111 A | 8/2000 | Glantz |
| 6,123,686 A | 9/2000 | Olsen et al. |
| 6,123,690 A | 9/2000 | Mejslov ........................ 604/283 |
| 6,135,949 A | 10/2000 | Russo et al. |
| 6,142,150 A | 11/2000 | O'Mahoney |
| 6,165,154 A | 12/2000 | Gray et al. |
| 6,171,287 B1 | 1/2001 | Lynn et al. |
| 6,202,708 B1 | 3/2001 | Bynum |
| 6,206,856 B1 | 3/2001 | Mahurkar |
| 6,211,856 B1 | 4/2001 | Choi et al. |
| 6,216,795 B1 | 4/2001 | Buchl |
| 6,225,711 B1 | 5/2001 | Gupta et al. |
| 6,241,704 B1 | 6/2001 | Peterson et al. |
| 6,246,992 B1 | 6/2001 | Brown |
| 6,248,093 B1 | 6/2001 | Moberg ........................ 604/131 |
| 6,253,804 B1 | 7/2001 | Safabash |
| 6,254,586 B1 | 7/2001 | Mann et al. |
| 6,259,587 B1 | 7/2001 | Sheldon et al. |
| 6,267,564 B1 | 7/2001 | Rapheal |
| 6,269,340 B1 | 7/2001 | Ford et al. |
| 6,270,455 B1 | 8/2001 | Brown |
| 6,280,416 B1 | 8/2001 | Van Antwerp et al. |
| 6,283,943 B1 | 9/2001 | Dy et al. |
| 6,293,159 B1 | 9/2001 | Kriesel et al. |
| 6,293,925 B1 | 9/2001 | Safabash et al. |
| 6,305,908 B1 | 10/2001 | Hermann et al. |
| 6,309,375 B1 | 10/2001 | Glines et al. |
| 6,311,868 B1 | 11/2001 | Krietemeier et al. |
| 6,321,158 B1 | 11/2001 | DeLorme et al. |
| 6,362,591 B1 | 3/2002 | Moberg |
| 6,364,859 B1 | 4/2002 | St. Romain et al. |
| 6,364,865 B1 | 4/2002 | Lavi et al. |
| 6,374,876 B2 | 4/2002 | Bynum |
| 6,375,638 B2 | 4/2002 | Nason et al. |
| 6,416,293 B1 | 7/2002 | Bouchard et al. |
| 6,422,057 B1 | 7/2002 | Anderson |
| 6,423,035 B1 | 7/2002 | Das et al. |
| 6,427,088 B1 | 7/2002 | Bowman, IV et al. |
| 6,428,509 B1 | 8/2002 | Fielder |
| 6,447,481 B1 | 9/2002 | Duchon et al. |
| 6,453,956 B2 | 9/2002 | Safabash |
| 6,458,102 B1 | 10/2002 | Mann et al. |
| 6,459,424 B1 | 10/2002 | Resman |
| 6,461,329 B1 | 10/2002 | Van Antwerp et al. |
| 6,461,331 B1 | 10/2002 | Van Antwerp |
| 6,466,203 B2 | 10/2002 | Van Ee |
| 6,475,180 B2 | 11/2002 | Peterson et al. |
| 6,475,196 B1 | 11/2002 | Vachon |
| 6,485,461 B1 | 11/2002 | Mason et al. |
| 6,485,465 B2 | 11/2002 | Moberg et al. |
| 6,520,938 B1 | 2/2003 | Funderburk et al. |
| 6,537,268 B1 | 3/2003 | Gibson et al. |
| 6,549,423 B1 | 4/2003 | Brodnick |
| 6,551,276 B1 | 4/2003 | Mann et al. |
| 6,551,277 B1 | 4/2003 | Ford |
| 6,554,798 B1 | 4/2003 | Mann et al. |
| 6,554,800 B1 | 4/2003 | Nezhadian et al. |
| 6,555,986 B2 | 4/2003 | Moberg |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,023 B1 | 5/2003 | Marrs et al. |
| 6,564,105 B2 | 5/2003 | Starkweather et al. |
| 6,571,128 B2 | 5/2003 | Lebel et al. |
| 6,572,542 B1 | 6/2003 | Houben et al. |
| 6,572,586 B1 | 6/2003 | Wojcik |
| 6,577,899 B2 | 6/2003 | Lebel et al. |
| RE38,189 E | 7/2003 | Walker et al. |
| 6,585,644 B2 | 7/2003 | Lebel et al. |
| 6,585,695 B1 | 7/2003 | Adair et al. |
| 6,591,876 B2 | 7/2003 | Safabash |
| 6,592,551 B1 | 7/2003 | Cobb |
| 6,595,756 B2 | 7/2003 | Gray et al. |
| 6,607,509 B2 | 8/2003 | Bobroff et al. |
| 6,613,015 B2 | 9/2003 | Sandstrom et al. |
| D480,477 S | 10/2003 | Bush et al. |
| 6,641,533 B2 | 11/2003 | Causey, III et al. |
| 6,642,936 B2 | 11/2003 | Engholm et al. |
| 6,645,177 B1 | 11/2003 | Shearn ........................ 604/155 |
| 6,648,821 B2 | 11/2003 | Lebel et al. |
| 6,652,493 B1 | 11/2003 | Das |
| 6,652,510 B2 | 11/2003 | Lord et al. |
| 6,656,148 B2 | 12/2003 | Das et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,665,909 B2 | 12/2003 | Collins et al. |
| 6,669,669 B2 | 12/2003 | Flaherty et al. |
| 6,684,058 B1 | 1/2004 | Karacaoglu et al. |
| 6,685,678 B2 | 2/2004 | Evans et al. |
| 6,687,546 B2 | 2/2004 | Lebel et al. |
| 6,689,091 B2 | 2/2004 | Bui et al. |
| 6,691,043 B2 | 2/2004 | Ribeiro, Jr. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,704,034 B1 | 3/2004 | Rodriguez et al. |
| 6,716,195 B2 | 4/2004 | Nolan, Jr. et al. |
| 6,723,072 B2 | 4/2004 | Flaherty et al. |
| 6,733,446 B2 | 5/2004 | Lebel et al. |
| 6,740,059 B2 | 5/2004 | Flaherty |
| 6,740,072 B2 | 5/2004 | Starkweather et al. |
| 6,740,075 B2 | 5/2004 | Lebel et al. |
| 6,743,205 B2 | 6/2004 | Nolan, Jr. et al. |
| 6,744,350 B2 | 6/2004 | Blomquist |
| 6,749,586 B2 | 6/2004 | Vasko |
| 6,749,587 B2 | 6/2004 | Flaherty |
| 6,752,299 B2 | 6/2004 | Shetler et al. |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,770,067 B2 | 8/2004 | Lorenzen et al. |
| 6,772,650 B2 | 8/2004 | Ohyama et al. |
| 6,800,071 B1 | 10/2004 | McConnell et al. |
| 6,801,420 B2 | 10/2004 | Talbot et al. |
| 6,805,693 B2 | 10/2004 | Gray et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,817,990 B2 | 11/2004 | Yap et al. |
| 6,827,702 B2 | 12/2004 | Lebel et al. |
| 6,830,558 B2 | 12/2004 | Flaherty et al. |
| 6,835,190 B2 | 12/2004 | Nguyen |
| 6,845,465 B2 | 1/2005 | Hashemi |
| 6,852,104 B2 | 2/2005 | Blomquist |
| 6,854,620 B2 | 2/2005 | Ramey |
| 6,872,200 B2 | 3/2005 | Mann et al. |
| 6,873,268 B2 | 3/2005 | Lebel et al. |
| 6,879,930 B2 | 4/2005 | Sinclair et al. |
| 6,902,207 B2 | 6/2005 | Lickliter |
| 6,916,010 B2 | 7/2005 | Beck et al. |
| 6,930,602 B2 | 8/2005 | Villaseca et al. |
| 6,932,584 B2 | 8/2005 | Gray et al. |
| 6,936,029 B2 | 8/2005 | Mann et al. |

(56) References Cited

U.S. PATENT DOCUMENTS

| | | |
|---|---|---|
| 6,945,760 B2 | 9/2005 | Gray et al. |
| 6,950,708 B2 | 9/2005 | Bowman IV et al. |
| 6,951,551 B2 | 10/2005 | Hudon |
| 6,958,705 B2 | 10/2005 | Lebel et al. |
| 6,960,192 B1 | 11/2005 | Flaherty et al. |
| 6,960,195 B2 | 11/2005 | Heinz et al. |
| 6,964,643 B2 | 11/2005 | Hovland et al. |
| 6,974,437 B2 | 12/2005 | Lebel et al. |
| 6,978,517 B2 | 12/2005 | Collins et al. |
| 6,979,326 B2 | 12/2005 | Mann et al. |
| 6,994,619 B2 | 2/2006 | Scholten |
| 6,997,905 B2 | 2/2006 | Gillespie, Jr. et al. |
| 6,997,907 B2 | 2/2006 | Safabash et al. |
| 6,997,910 B2 | 2/2006 | Howlett et al. |
| 6,997,920 B2 | 2/2006 | Mann et al. |
| 6,997,921 B2 | 2/2006 | Gray et al. |
| 6,999,854 B2 | 2/2006 | Roth |
| 7,011,608 B2 | 3/2006 | Spencer |
| 7,018,360 B2 | 3/2006 | Flaherty et al. |
| 7,021,560 B2 | 4/2006 | Gray et al. |
| 7,024,245 B2 | 4/2006 | Lebel et al. |
| 7,025,226 B2 | 4/2006 | Ramey |
| 7,025,743 B2 | 4/2006 | Mann et al. |
| 7,029,455 B2 | 4/2006 | Flaherty |
| 7,029,456 B2 | 4/2006 | Ware et al. |
| 7,033,338 B2 | 4/2006 | Vilks et al. |
| 7,033,339 B1 | 4/2006 | Lynn |
| 7,041,082 B2 | 5/2006 | Blomquist et al. |
| 7,045,361 B2 | 5/2006 | Heiss et al. |
| 7,046,230 B2 | 5/2006 | Zadesky et al. |
| 7,050,927 B2 | 5/2006 | Sinclair et al. |
| 7,052,251 B2 | 5/2006 | Nason et al. |
| 7,052,483 B2 | 5/2006 | Wojcik |
| 7,061,140 B2 | 6/2006 | Zhang et al. |
| 7,063,684 B2 | 6/2006 | Moberg |
| 7,066,029 B2 | 6/2006 | Beavis et al. |
| 7,074,209 B2 | 7/2006 | Evans et al. |
| 7,075,512 B1 | 7/2006 | Fabre et al. |
| 7,098,803 B2 | 8/2006 | Mann et al. |
| 7,109,878 B2 | 9/2006 | Mann et al. |
| 7,113,821 B1 | 9/2006 | Sun et al. |
| 7,115,113 B2 | 10/2006 | Evans et al. |
| 7,131,967 B2 | 11/2006 | Gray et al. |
| 7,137,964 B2 | 11/2006 | Flaherty |
| 7,144,384 B2 | 12/2006 | Gorman et al. |
| 7,146,977 B2 | 12/2006 | Beavis et al. |
| 7,278,983 B2 | 10/2007 | Ireland et al. |
| 7,303,549 B2 | 12/2007 | Flaherty et al. |
| 7,305,984 B2 | 12/2007 | Altobelli et al. |
| 7,306,578 B2 * | 12/2007 | Gray et al. ............ 604/151 |
| 7,342,660 B2 | 3/2008 | Altobelli et al. |
| 7,390,314 B2 | 6/2008 | Stutz, Jr. et al. |
| 7,498,563 B2 | 3/2009 | Mandro et al. |
| 7,682,338 B2 | 3/2010 | Griffin |
| 7,806,868 B2 | 10/2010 | De Polo et al. |
| 7,927,314 B2 | 4/2011 | Kuracina et al. |
| 8,016,789 B2 | 9/2011 | Grant et al. |
| 8,034,026 B2 * | 10/2011 | Grant et al. ............ 604/121 |
| 8,108,040 B2 | 1/2012 | Bernard et al. |
| 8,262,616 B2 * | 9/2012 | Grant et al. ............ 604/151 |
| 2001/0031944 A1 | 10/2001 | Peterson et al. |
| 2001/0034502 A1 | 10/2001 | Moberg et al. |
| 2001/0041869 A1 | 11/2001 | Causey, III et al. |
| 2001/0056258 A1 | 12/2001 | Evans |
| 2002/0002326 A1 | 1/2002 | Causey, III et al. |
| 2002/0013613 A1 | 1/2002 | Haller et al. |
| 2002/0022807 A1 | 2/2002 | Duchon et al. |
| 2002/0038392 A1 | 3/2002 | De La Huerga |
| 2002/0043951 A1 | 4/2002 | Moberg |
| 2002/0052539 A1 | 5/2002 | Haller et al. |
| 2002/0052574 A1 | 5/2002 | Hochman et al. |
| 2002/0056114 A1 | 5/2002 | Fillebrown et al. |
| 2002/0077598 A1 | 6/2002 | Yap et al. |
| 2002/0077852 A1 | 6/2002 | Ford et al. |
| 2002/0082665 A1 | 6/2002 | Haller et al. |
| 2002/0091454 A1 | 7/2002 | Vasko |
| 2002/0107481 A1 | 8/2002 | Reilly et al. |
| 2002/0123672 A1 | 9/2002 | Christophersom et al. |
| 2002/0126036 A1 | 9/2002 | Flaherty et al. |
| 2002/0143290 A1 | 10/2002 | Bui et al. |
| 2002/0158838 A1 | 10/2002 | Smith et al. |
| 2002/0169439 A1 | 11/2002 | Flaherty |
| 2002/0173748 A1 * | 11/2002 | McConnell et al. ..... 604/167.02 |
| 2002/0193679 A1 | 12/2002 | Malave et al. |
| 2002/0193846 A1 | 12/2002 | Pool et al. |
| 2003/0009133 A1 * | 1/2003 | Ramey ............ 604/155 |
| 2003/0014013 A1 | 1/2003 | Choi |
| 2003/0028079 A1 | 2/2003 | Lebel et al. |
| 2003/0028346 A1 | 2/2003 | Sinclair et al. |
| 2003/0065308 A1 | 4/2003 | Lebel et al. |
| 2003/0069543 A1 | 4/2003 | Carpenter et al. |
| 2003/0076306 A1 | 4/2003 | Zadesky et al. |
| 2003/0088238 A1 | 5/2003 | Poulsen et al. |
| 2003/0114836 A1 | 6/2003 | Estes et al. |
| 2003/0125672 A1 | 7/2003 | Adair et al. |
| 2003/0130618 A1 | 7/2003 | Gray et al. |
| 2003/0132922 A1 | 7/2003 | Philipp |
| 2003/0141981 A1 | 7/2003 | Bui et al. |
| 2003/0161744 A1 | 8/2003 | Vilks et al. |
| 2003/0163089 A1 | 8/2003 | Bynum |
| 2003/0163090 A1 | 8/2003 | Blomquist et al. |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0212364 A1 | 11/2003 | Mann et al. |
| 2003/0212379 A1 | 11/2003 | Bylund et al. |
| 2003/0229311 A1 | 12/2003 | Morris et al. |
| 2003/0233069 A1 | 12/2003 | Gillespie, Jr. et al. |
| 2004/0003493 A1 | 1/2004 | Adair et al. |
| 2004/0054326 A1 | 3/2004 | Hommann et al. |
| 2004/0059315 A1 | 3/2004 | Erickson et al. |
| 2004/0064088 A1 | 4/2004 | Gorman et al. |
| 2004/0068230 A1 | 4/2004 | Estes et al. |
| 2004/0073095 A1 | 4/2004 | Causey, III et al. |
| 2004/0073161 A1 | 4/2004 | Tachibana |
| 2004/0082908 A1 | 4/2004 | Whitehurst et al. |
| 2004/0082918 A1 | 4/2004 | Evans et al. |
| 2004/0085215 A1 | 5/2004 | Moberg et al. |
| 2004/0092873 A1 | 5/2004 | Moberg |
| 2004/0092878 A1 | 5/2004 | Flaherty |
| 2004/0116893 A1 | 6/2004 | Spohn et al. |
| 2004/0121767 A1 | 6/2004 | Simpson et al. |
| 2004/0127958 A1 | 7/2004 | Mazar et al. |
| 2004/0133166 A1 | 7/2004 | Moberg et al. |
| 2004/0135078 A1 | 7/2004 | Mandro et al. |
| 2004/0140304 A1 | 7/2004 | Leyendecker |
| 2004/0158193 A1 | 8/2004 | Bui et al. |
| 2004/0162528 A1 | 8/2004 | Horvath et al. |
| 2004/0167464 A1 | 8/2004 | Ireland et al. |
| 2004/0172301 A1 | 9/2004 | Mihai et al. |
| 2004/0176667 A1 | 9/2004 | Mihai et al. |
| 2004/0176725 A1 | 9/2004 | Stutz, Jr. et al. |
| 2004/0193090 A1 | 9/2004 | Lebel et al. |
| 2004/0207404 A1 | 10/2004 | Zhang et al. |
| 2004/0235446 A1 | 11/2004 | Flaherty et al. |
| 2004/0243065 A1 | 12/2004 | McConnell et al. |
| 2005/0015056 A1 | 1/2005 | Duchon et al. |
| 2005/0021000 A1 | 1/2005 | Adair et al. |
| 2005/0022274 A1 | 1/2005 | Campbell et al. |
| 2005/0027254 A1 | 2/2005 | Vasko |
| 2005/0035956 A1 | 2/2005 | Sinclair et al. |
| 2005/0048900 A1 | 3/2005 | Scholten |
| 2005/0052429 A1 | 3/2005 | Philipp |
| 2005/0055242 A1 | 3/2005 | Bello et al. |
| 2005/0055244 A1 | 3/2005 | Mullan et al. |
| 2005/0062732 A1 | 3/2005 | Sinclair et al. |
| 2005/0063857 A1 | 3/2005 | Alheidt et al. |
| 2005/0065464 A1 | 3/2005 | Talbot et al. |
| 2005/0065817 A1 | 3/2005 | Mihai et al. |
| 2005/0069425 A1 | 3/2005 | Gray et al. |
| 2005/0085760 A1 | 4/2005 | Ware et al. |
| 2005/0096593 A1 | 5/2005 | Pope et al. |
| 2005/0137530 A1 | 6/2005 | Campbell et al. |
| 2005/0137573 A1 | 6/2005 | McLaughlin |

(56) References Cited

U.S. PATENT DOCUMENTS

| | | |
|---|---|---|
| 2005/0148938 A1 | 7/2005 | Blomquist |
| 2005/0171512 A1 | 8/2005 | Flaherty |
| 2005/0171513 A1 | 8/2005 | Mann et al. |
| 2005/0177111 A1 | 8/2005 | Ozeri et al. |
| 2005/0182366 A1 | 8/2005 | Vogt et al. |
| 2005/0182389 A1 | 8/2005 | LaPorte et al. |
| 2005/0187515 A1 | 8/2005 | Varrichio et al. |
| 2005/0187593 A1 | 8/2005 | Housworth et al. |
| 2005/0192494 A1 | 9/2005 | Ginsberg |
| 2005/0203461 A1 | 9/2005 | Flaherty et al. |
| 2005/0215982 A1 | 9/2005 | Malave et al. |
| 2005/0224705 A1 | 10/2005 | Tobiason et al. |
| 2005/0234404 A1 | 10/2005 | Vilks et al. |
| 2005/0238503 A1 | 10/2005 | Rush et al. |
| 2005/0238507 A1 | 10/2005 | DiIanni et al. |
| 2005/0245904 A1 | 11/2005 | Estes et al. |
| 2005/0250368 A1 | 11/2005 | Singer et al. |
| 2005/0261660 A1 | 11/2005 | Choi |
| 2005/0263615 A1 | 12/2005 | Kriesel et al. |
| 2005/0267363 A1 | 12/2005 | Duchon et al. |
| 2005/0267550 A1 | 12/2005 | Hess et al. |
| 2005/0267928 A1 | 12/2005 | Anderson et al. |
| 2005/0273059 A1 | 12/2005 | Mernoe et al. |
| 2005/0285880 A1 | 12/2005 | Lai et al. |
| 2006/0016800 A1 | 1/2006 | Paradiso et al. |
| 2006/0025663 A1 | 2/2006 | Talbot et al. |
| 2006/0026535 A1 | 2/2006 | Hotelling et al. |
| 2006/0026536 A1 | 2/2006 | Hotelling et al. |
| 2006/0038791 A1 | 2/2006 | Mackey |
| 2006/0041229 A1 | 2/2006 | Garibotto et al. |
| 2006/0065772 A1 | 3/2006 | Grant et al. |
| 2006/0066581 A1 | 3/2006 | Lyon et al. |
| 2006/0097991 A1 | 5/2006 | Hotelling et al. |
| 2006/0100591 A1 | 5/2006 | Alheidt et al. |
| 2006/0106346 A1 | 5/2006 | Sullivan et al. |
| 2006/0123884 A1 | 6/2006 | Selker et al. |
| 2006/0129112 A1 | 6/2006 | Lynn |
| 2006/0144942 A1 | 7/2006 | Evans et al. |
| 2006/0160670 A1 | 7/2006 | Spencer |
| 2006/0161870 A1 | 7/2006 | Hotelling et al. |
| 2006/0161871 A1 | 7/2006 | Hotelling et al. |
| 2006/0173406 A1 | 8/2006 | Hayes et al. |
| 2006/0173444 A1 | 8/2006 | Choy et al. |
| 2006/0178633 A1 | 8/2006 | Garibotto et al. |
| 2006/0178836 A1 | 8/2006 | Bai et al. |
| 2006/0184084 A1 | 8/2006 | Ware et al. |
| 2006/0184123 A1 | 8/2006 | Gillespie et al. |
| 2006/0184154 A1 | 8/2006 | Moberg et al. |
| 2006/0200257 A1 | 9/2006 | Kirste et al. |
| 2006/0227117 A1 | 10/2006 | Proctor |
| 2006/0229557 A1 | 10/2006 | Fathallah et al. |
| 2006/0232554 A1 | 10/2006 | Wong et al. |
| 2006/0236262 A1 | 10/2006 | Bathiche et al. |
| 2006/0236263 A1 | 10/2006 | Bathiche et al. |
| 2006/0253085 A1 | 11/2006 | Geismar et al. |
| 2006/0264894 A1 | 11/2006 | Moberg et al. |
| 2006/0282290 A1 | 12/2006 | Flaherty et al. |
| 2007/0049870 A1 | 3/2007 | Gray et al. |
| 2007/0060872 A1 | 3/2007 | Hall et al. |
| 2007/0062250 A1 | 3/2007 | Krulevitch et al. |
| 2007/0066940 A1 | 3/2007 | Karunaratne et al. |
| 2007/0066956 A1 | 3/2007 | Finkel |
| 2007/0072146 A1 | 3/2007 | Pierson |
| 2007/0093750 A1 | 4/2007 | Jan et al. |
| 2007/0100283 A1 | 5/2007 | Causey, III et al. |
| 2007/0112298 A1 | 5/2007 | Mueller, Jr. et al. |
| 2007/0118405 A1 | 5/2007 | Campbell et al. |
| 2007/0161955 A1 | 7/2007 | Bynum et al. |
| 2007/0167905 A1 | 7/2007 | Estes et al. |
| 2007/0178776 A1 | 8/2007 | Etter et al. |
| 2007/0191770 A1 | 8/2007 | Moberg et al. |
| 2007/0203439 A1 | 8/2007 | Boyd et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0228071 A1 | 10/2007 | Kamen et al. |
| 2007/0255250 A1 | 11/2007 | Moberg et al. |
| 2007/0258395 A1 | 11/2007 | Jollota et al. |
| 2008/0009824 A1 | 1/2008 | Moberg et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0097321 A1 | 4/2008 | Mounce et al. |
| 2008/0097327 A1 | 4/2008 | Bente et al. |
| 2008/0097328 A1 | 4/2008 | Moberg et al. |
| 2008/0097381 A1 | 4/2008 | Moberg et al. |
| 2008/0125700 A1 | 5/2008 | Moberg et al. |
| 2008/0125701 A1 | 5/2008 | Moberg et al. |
| 2008/0160492 A1 | 7/2008 | Campbell et al. |
| 2008/0161754 A1 | 7/2008 | Marano-Ford |
| 2008/0177900 A1 | 7/2008 | Grant et al. |
| 2008/0243079 A1 | 10/2008 | Wooley et al. |
| 2008/0255502 A1 | 10/2008 | Jacobson et al. |
| 2008/0294108 A1 | 11/2008 | Briones et al. |
| 2009/0036870 A1 | 2/2009 | Mounce et al. |
| 2009/0062767 A1 | 3/2009 | Van Antwerp et al. |
| 2009/0062778 A1 | 3/2009 | Bengtsson et al. |
| 2009/0069749 A1 | 3/2009 | Miller et al. |
| 2009/0076461 A1 | 3/2009 | Susi et al. |
| 2009/0099523 A1 | 4/2009 | Grant et al. |
| 2009/0124994 A1 | 5/2009 | Roe |
| 2009/0139517 A1 | 6/2009 | Wachtel et al. |
| 2009/0143735 A1 | 6/2009 | De Polo et al. |
| 2009/0160654 A1 | 6/2009 | Yang |
| 2009/0163855 A1 | 6/2009 | Shin et al. |
| 2009/0164251 A1 | 6/2009 | Hayter |
| 2009/0171291 A1 | 7/2009 | Bente, IV et al. |
| 2009/0172425 A1 | 7/2009 | Cetin et al. |
| 2009/0198183 A1 | 8/2009 | Krumme et al. |
| 2009/0234213 A1 | 9/2009 | Hayes et al. |
| 2009/0254025 A1 | 10/2009 | Simmons |
| 2009/0259217 A1 | 10/2009 | Hyde et al. |
| 2009/0270811 A1 | 10/2009 | Mounce et al. |
| 2010/0022963 A1 | 1/2010 | Edwards et al. |
| 2010/0063445 A1 | 3/2010 | Sternberg et al. |
| 2010/0186739 A1 | 7/2010 | Kronestedt et al. |
| 2010/0305512 A1 | 12/2010 | Guillermo et al. |
| 2011/0208123 A1 | 8/2011 | Gray et al. |

FOREIGN PATENT DOCUMENTS

| | | |
|---|---|---|
| DE | 201 10 059 U1 | 9/2002 |
| EP | 0 256 694 A1 | 2/1988 |
| EP | 0 258 566 A2 | 3/1988 |
| EP | 0338671 A1 | 10/1989 |
| EP | 0554995 B1 | 8/1993 |
| EP | 0 398 394 | 10/1993 |
| EP | 0 749 757 A2 | 12/1996 |
| EP | 0763368 A2 | 3/1997 |
| EP | 0806738 A1 | 11/1997 |
| EP | 0830597 B1 | 3/1998 |
| EP | 0917882 A1 | 5/1999 |
| EP | 1007137 B1 | 6/2000 |
| EP | 1109586 B1 | 6/2001 |
| EP | 1177802 A1 | 2/2002 |
| EP | 1338295 A1 | 8/2003 |
| EP | 1473050 A1 | 3/2004 |
| EP | 1115435 B1 | 8/2005 |
| EP | 1347705 B1 | 12/2005 |
| EP | 1688085 A1 | 8/2006 |
| EP | 1839694 A1 | 10/2007 |
| GB | 2218831 A | 11/1989 |
| WO | 94/08647 A1 | 4/1994 |
| WO | 95/24229 A2 | 9/1995 |
| WO | 95/28878 A1 | 11/1995 |
| WO | 95/31233 A1 | 11/1995 |
| WO | 96/08281 A1 | 3/1996 |
| WO | 96/14100 A1 | 5/1996 |
| WO | 96/20745 A1 | 7/1996 |
| WO | 96/36389 A1 | 11/1996 |
| WO | 97/21456 A1 | 6/1997 |
| WO | 97/40482 A1 | 10/1997 |
| WO | 98/14234 A1 | 4/1998 |
| WO | 98/17336 A1 | 4/1998 |

(56) References Cited

FOREIGN PATENT DOCUMENTS

| | | |
|---|---|---|
| WO | 98/20439 A1 | 5/1998 |
| WO | 98/24358 A2 | 6/1998 |
| WO | 98/42407 A1 | 10/1998 |
| WO | 98/49659 A2 | 11/1998 |
| WO | 98/59487 A1 | 12/1998 |
| WO | 9858693 A1 | 12/1998 |
| WO | 99/08183 A1 | 2/1999 |
| WO | 99/10801 A1 | 3/1999 |
| WO | 99/18532 A1 | 4/1999 |
| WO | 99/22236 A1 | 5/1999 |
| WO | WO 99/44655 | 9/1999 |
| WO | 99/59663 A1 | 11/1999 |
| WO | 00/10628 A2 | 3/2000 |
| WO | 00/28217 A1 | 5/2000 |
| WO | 0069493 A1 | 11/2000 |
| WO | 01/00261 A1 | 1/2001 |
| WO | 01/61616 A3 | 8/2001 |
| WO | 01/70304 A1 | 9/2001 |
| WO | 02/04047 A2 | 1/2002 |
| WO | 02/24257 A1 | 3/2002 |
| WO | 02/49509 A2 | 6/2002 |
| WO | 02/056945 A2 | 7/2002 |
| WO | WO 02/053220 A2 | 7/2002 |
| WO | 02/070049 A1 | 9/2002 |
| WO | 02/083209 A1 | 10/2002 |
| WO | 03/053498 A2 | 7/2003 |
| WO | 03/059422 A1 | 7/2003 |
| WO | 03/063932 A2 | 8/2003 |
| WO | 03/071930 A2 | 9/2003 |
| WO | 03/090838 A1 | 11/2003 |
| WO | 03/094075 A1 | 11/2003 |
| WO | 2004/007133 A1 | 1/2004 |
| WO | 2004/008956 A2 | 1/2004 |
| WO | 2004/009160 A1 | 1/2004 |
| WO | 2004006981 A2 | 1/2004 |
| WO | 2004-028596 A1 | 4/2004 |
| WO | 2004/058327 A2 | 7/2004 |
| WO | 2004/069095 A2 | 8/2004 |
| WO | 2004/070548 A2 | 8/2004 |
| WO | 2004/070557 A2 | 8/2004 |
| WO | 2004/070994 A2 | 8/2004 |
| WO | 2004/070995 A2 | 8/2004 |
| WO | 2004/098390 A2 | 11/2004 |
| WO | 2005/000378 A2 | 1/2005 |
| WO | 2005/010796 A2 | 2/2005 |
| WO | 2005/016411 A2 | 2/2005 |
| WO | 2005/019766 A2 | 3/2005 |
| WO | 2005/019987 A2 | 3/2005 |
| WO | 2005/039671 A2 | 5/2005 |
| WO | 2005/094920 A1 | 10/2005 |
| WO | 2005/101279 A2 | 10/2005 |
| WO | 2005-102416 A1 | 11/2005 |
| WO | 2005/112899 A2 | 12/2005 |
| WO | 2005/121938 A2 | 12/2005 |
| WO | 2006/001929 A1 | 1/2006 |
| WO | 2006/023147 A1 | 3/2006 |
| WO | 2006/032652 A1 | 3/2006 |
| WO | 2006/081975 A1 | 8/2006 |
| WO | 2006/083831 A1 | 8/2006 |
| WO | 2006/097453 A1 | 9/2006 |
| WO | 2006/108809 A1 | 10/2006 |
| WO | 2007/016145 A1 | 2/2007 |
| WO | 2007/094833 A1 | 8/2007 |
| WO | 2009/083600 A1 | 7/2009 |

OTHER PUBLICATIONS

Search Report from corresponding EP Appln. No. 10075446.4 dated Aug. 25, 2011 (10 pages).
Search Report from corresponding International Appln. No. PCT/US2011/030553 dated Dec. 23, 2011 (12 pages).
Preliminary Report on Patentability from corresponding International Appln. No. PCT/US2011/022051 dated Jul. 24, 2012 (13 pages).
Extended European Search Report, dated Mar. 5, 2010, received in European Patent Application No. 09075460.7, 14 pgs.
International Search Report and Written Opinion From Corresponding International Application No. PCT/US2007/003490, dated Nov. 28, 2007 (20 pages).
International Search Report and Written Opinion From Corresponding International Application No. PCT/US2007/003567, dated Oct. 17, 2007 (18 pages).
International Search Report and Written Opinion From Corresponding International Application No. PCT/US2007/003587, Nov. 12, 2007 (18 pages).
International Search Report and Written Opinion From Corresponding International Application No. PCT/US2007/003634, Oct. 2, 2007 (18 pages).
Conical fittings with a 6% (Luer) taper for syringes, needles and certain other medical equipment—Lock fittings, British Standard, BS EN 1707: 1997 (20 pages).
Conical fittings with a 6% (Luer) taper for syringes, needles and certain other medical equipment, Part 1. General requirements, British Standard, BS EN 20594-1 : 1994 ISO 594-1 : 1986 (17 pages).
International Preliminary Report on Patentability From Corresponding International Application No. PCT/US2007/003567, dated Aug. 21, 2008 (11 pages).
International Search Report From Corresponding International Application No. PCT/US2009/060158, dated Mar. 23, 2010 (7 pages).
International Search Report and Written Opinion From Corresponding International Application No. PCT/US2009/093169, dated Mar. 31, 2010 (23 pages).
Non-final Office Action from corresponding U.S. Appl. No. 12/249,891, dated Nov. 18, 2009 (15 pages).

* cited by examiner

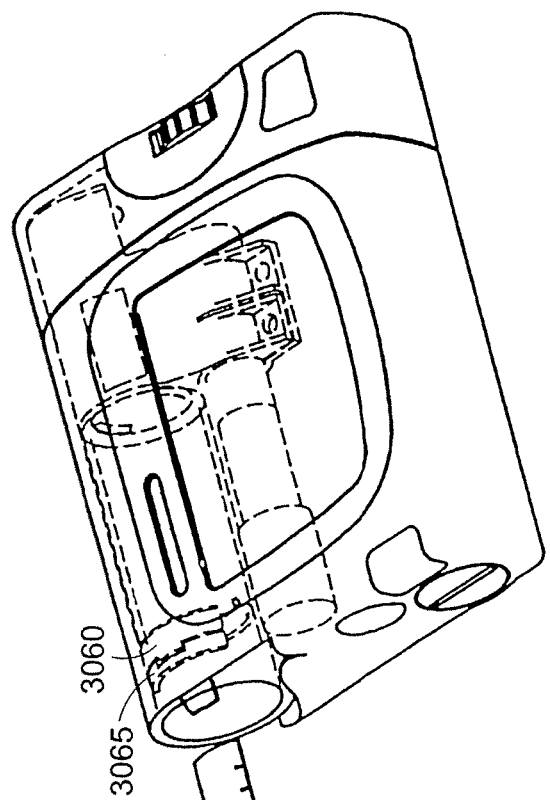
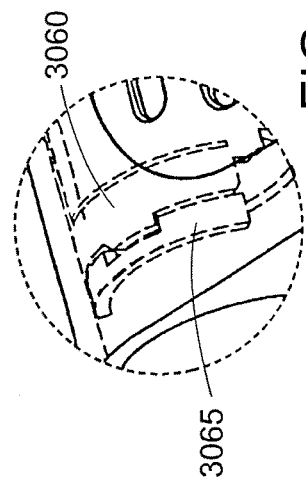
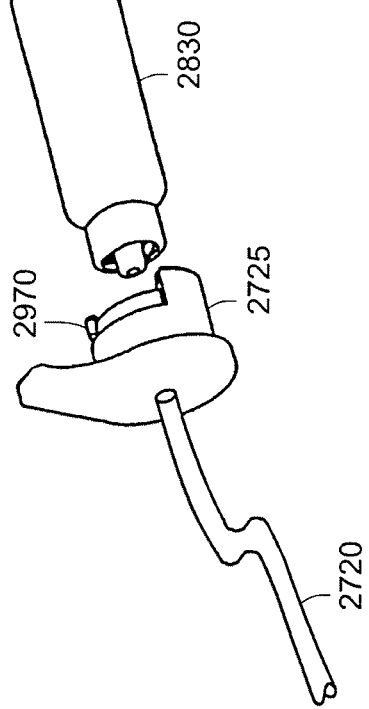
FIG. 29
FIG. 30

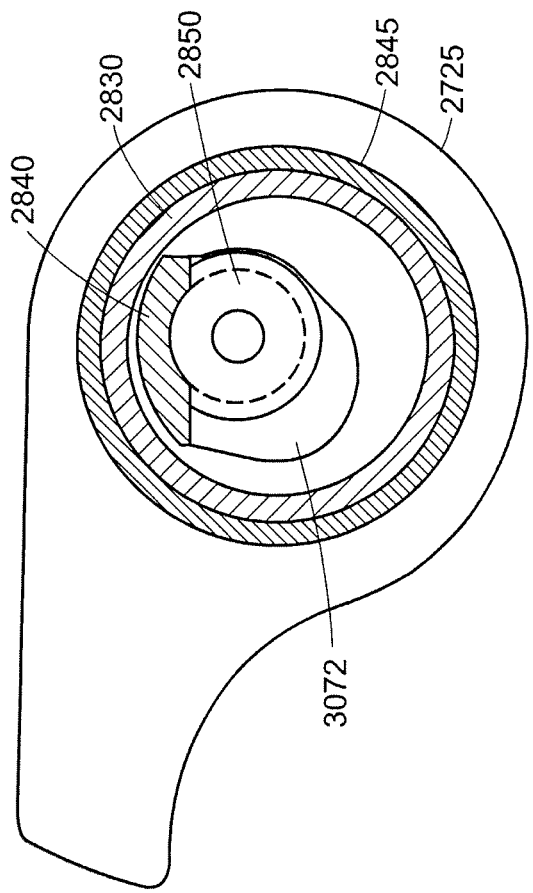
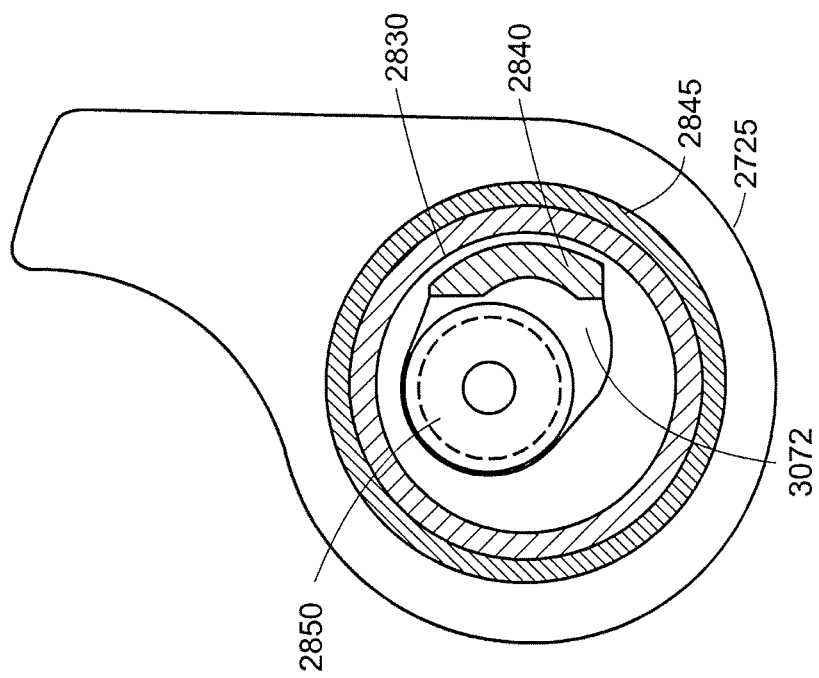
FIG. 32
FIG. 31

INFUSION SET FOR A FLUID PUMP

This application is a continuation of U.S. patent application Ser. No. 10/151,733, filed May 20, 2002, entitled "Infusion Set for a Fluid Pump," which application is a continuation-in-part of U.S. patent application Ser. No. 10/037,614, filed Jan. 4, 2002, and entitled "Loading Mechanism for Infusion Pump." This application also claims priority from U.S. provisional patent application Ser. No. 60/291,881, filed May 18, 2001, entitled "Cannula Designs for Insulin Pump Systems." Each of these patent applications described in this paragraph is hereby incorporated by reference, in its entirety.

TECHNICAL FIELD AND BACKGROUND ART

The present invention relates to a system and method for delivery of a fluid to a patient, and more particularly, to an infusion set for a fluid pump that may be used, for example, to deliver insulin to a patient.

Currently, there are two primary methods of treating diabetes. One method involves taking multiple injections of long acting insulin on a daily basis. The second method is by continuous delivery of short acting insulin to more closely emulate the human pancreas. This may be accomplished using a syringe pump.

A syringe pump typically includes four major components. These components are a microprocessor controlled syringe pump, an insulin filled syringe, a hub and tubing set, and a cannula.

A syringe pump is often worn in a carrying case on a patient's belt, in a manner similar to a pager, or in more discrete locations such as a pocket or a brassiere. The syringe is mounted in the syringe pump and may hold enough insulin for three days. The hub serves as an interface between the syringe and a tubing set. At the end of a tubing set is a cannula typically made of either steel or Teflon. The cannula may advantageously be carried in a cannula assembly. The cannula assembly typically attaches to the patient by adhesive and is placed near the abdomen around and to the side of the navel. The cannula is inserted in fatty tissue and the insulin is injected subcutaneously.

A patient may perform activities that do not permit or are hindered by the presence of a pump, for example, when a patient wishes to take a shower or participate in certain athletic activities. Removing each of the components, including the cannula, would require a needle stick upon reconnecting the system to a patient. Since a needle stick is undesirable every time one wishes to take a shower or participate in sports, state of the art tubing sets disconnect at or near the cannula assembly, with the tubing capped to prevent contamination. Disconnecting and reconnecting the tubing set is sometimes difficult.

Cannulas with steel subcutaneous needles have been used with syringe pumps for decades. Steel needles, however, can cause irritation and discomfort. Soft cannulas, which may be made of Teflon, for example, help prevent this discomfort and are generally known in the art. The soft cannula requires the use of a steel insertion needle to penetrate skin and/or other tissue. When inserting the needle, the needle penetrates a first self-sealing septum in the cannula housing. The needle is then pushed through the soft cannula until it extends through the cannula's outer tip. After insertion of the needle into the skin, the steel needle is removed and the first septum seals the opening where the insertion needle entered. The tubing set may then be connected to the cannula by inserting a tubing needle at the end of the tubing set into a second septum in the cannula housing.

After removing the insertion needle, the first septum may be susceptible to leakage. This leakage may become more prevalent under pressure, such as when the cannula has an occlusion. Normally during an occlusion, the pressure will reach a threshold and trigger an alarm on the pump. However, if the first septum leaks, the pressure may never reach the threshold, and the pump may continue to deliver insulin. As a result, the insulin will continue to leak out of the first septum, the alarm will never trigger, and the user unknowingly does not receive the drug for an indefinite period of time.

SUMMARY OF THE INVENTION

In a first embodiment of the invention there is provided a medical device for delivery of a fluid to a patient from a line terminating in a tubing needle. The medical device includes a cannula assembly for coupling the fluid into a cannula that is inserted into the patient. The cannula assembly has a first locking element disposed in a fixed position with respect to the cannula. Coupling the line to the cannula assembly is an infusion flap. The infusion flap includes a second locking element for engaging the first locking element of the cannula assembly and a lift tab for disconnecting the infusion flap from the cannula assembly. Coupling of the first and second locking elements requires initial mating of the infusion flap and cannula assembly, followed by locking through rotation of the infusion flap with respect to the cannula assembly.

In a related embodiment, the cannula assembly may include a septum housing defining a core coupled to the cannula. The septum housing includes a first septum positioned within the core at a first position, such that when the infusion flap and the cannula assembly are locked, the tubing needle penetrates the first septum so as to permit fluid communication between the line and the cannula. The septum housing may also include a second septum positioned within the core at a second position, such that an insertion needle can be introduced through the second septum into the cannula.

In another related embodiment of the invention, the cannula assembly further includes a flexible tube in fluid communication with both the cannula and a septum. When the flexible tube is in a first position, an insertion needle can be introduced through the septum into the cannula, and when the flexible tube is in a second position, a tubing needle inserted through the septum permits fluid communication between the line and the cannula.

In yet another related embodiment of the invention, the device further includes an insertion flap. The insertion flap includes an insertion needle for inserting through the septum and terminating with a sharp distal end disposed slightly beyond a distal end of the cannula. The insertion flap has an interface for coupling to an auto-insertion device.

In other related embodiments, the first locking element may be a locking lug and the second locking element is a lug receptacle, or vice versa. The cannula assembly may include a soft overmolded body.

In accordance with another embodiment of the invention, a medical device for delivery of a fluid to a patient from a line terminating in a tubing needle is presented that includes a cannula for insertion into the patient. A flexible tube is in fluid communication with both the cannula and a septum. When the flexible tube is in a first position, an insertion needle can be introduced through the septum into the cannula, and when the flexible tube is in a second position, a tubing needle inserted through the septum permits fluid communication between the line and the cannula.

In accordance with related embodiments of the invention, the device further includes an infusion flap that includes the tubing needle and a cannula assembly that includes the cannula. When the infusion flap and cannula assembly are mated, the tubing needle passes through the septum permitting fluid communication between the line and the cannula. The device may further include a locking mechanism for securing the infusion flap to the cannula assembly. The locking mechanism may include a locking tang on the infusion flap, the locking tang inserted into a tang receptacle on the cannula assembly. As another example, the locking mechanism may include a first locking element disposed on a septum housing containing the septum, and a second locking element disposed on the infusion flap. Coupling the first and second locking elements may require initial mating of the infusion flap and cannula assembly followed by locking through rotation of the infusion flap with respect to the cannula assembly. In various embodiments, the first locking element is a locking lug and the second locking element is a lug receptacle, or vice versa. In various embodiments, the septum housing can be rotated to a mating position that allows the infusion flap and the septum housing to be mated together and the infusion flap rotated with respect to the cannula assembly to lock the infusion flap onto the septum housing. The septum housing can then be rotated to a stable position that prevents rotation of the infusion flap.

In accordance with another embodiment of the invention, a method for delivering a fluid to a patient from a line terminating in a tubing needle is presented. The method includes inserting an insertion needle through a septum and a cannula, the septum and the cannula having a relative orientation. The cannula is inserted into tissue of a patient. After withdrawing the insertion needle from the cannula and the septum, a tubing needle is inserted through the septum. The relative orientation between the septum and the cannula is varied and the fluid is delivered through the line and the cannula.

In accordance with still another embodiment of the invention, a tubing set for coupling a fluid delivery device containing a fluid source into fluid communication with a cannula assembly is presented. The tubing set includes a length of tubing having a first end and a second end. A hub is coupled to the first end for connecting to the fluid delivery device. The hub includes a controller which allows the fluid delivery device to transition from a first configuration to a second configuration. An infusion flap is coupled to the second end for connecting to the cannula assembly.

In another related embodiment of the invention, the first configuration of the fluid delivery device may be a reservoir load position and the second configuration may be an operate position. The controller may be capable of allowing the fluid delivery device to transition from the second configuration to the first configuration. The controller may include a flange that interfaces with the fluid delivery device. In other embodiments, the controller may include an electronic circuit to the fluid delivery device, or generating one of an optical signal and magnetic field. The hub may include a luer connector for mating with the fluid delivery device.

In another related embodiment of the invention, the fluid delivery device may be an infusion pump having a reservoir with variable volume and a drive assembly. The drive assembly includes a barrel having a clearance hole in a barrel end, the barrel characterized by a longitudinal barrel axis of rotation. The drive assembly further includes a plunger rod inserted through the clearance hole, and a rotating drive screw with external threads. The external threads removably engage with threads on the plunger rod by rotating the barrel about the barrel axis. The external threads are engaged with the threads on the plunger rod when in the first configuration and the external threads are disengaged with the threads on the plunger rod when in the second configuration. The controller is capable of allowing the barrel to rotate so as to bring the rod threads in and out of mechanical engagement with the drive screw threads. The controller may include a flange for dislodging a locking tab on the barrel, allowing the barrel to rotate.

In accordance with still another embodiment of the invention, a conduit for coupling to a fluid delivery device is presented. The conduit includes a length of tubing having a first end. A hub is coupled to the first end for connecting to the fluid delivery device. The hub includes a controller which allows the fluid delivery device to transition from a first configuration to a second configuration.

In related embodiments of the invention, the first configuration may be a reservoir load position and the second configuration may be an operate position. The hub may include a luer connector for mating with the fluid delivery device. The controller may include a flange that interfaces with the fluid delivery device. The controller may include an electronic circuit to the fluid delivery device, or generating one of an optical signal and magnetic field.

In still yet another embodiment of the invention, a method of providing flow of a fluid from a fluid delivery device to a porous medium is presented. The method includes coupling a hub, permanently affixed to a tube set, to the fluid delivery device. Configuration of the fluid delivery device is controlled via the hub. The tube set is coupled to the porous medium so as to allow fluid to flow from the fluid delivery device to the porous medium.

In related embodiments of the invention, controlling the configuration of the fluid delivery device may include allowing the pump to move from a first configuration to a second configuration. The first configuration of the fluid delivery device may be a load position and the second configuration may be an operate position. Controlling the configuration of the fluid delivery device may include moving a flange on the hub or generating one of a magnetic field and an optical signal. The fluid delivery device may be an infusion pump.

BRIEF DESCRIPTION OF THE DRAWINGS

The foregoing features of the invention will be more readily understood by reference to the following detailed description, taken with reference to the accompanying drawings, in which:

FIG. 29 shows an embodiment of a pump barrel locking mechanism of FIG. 27;

FIG. 30 is an exploded view of the pump barrel locking mechanism of FIG. 27;

FIG. 31 shows the relation of the drive screw to the plunger rod for the infusion pump of FIG. 27 when in a loading position;

FIG. 32 shows the relation of the drive screw to the plunger rod for the infusion pump of FIG. 27 when in an engaged position;

DETAILED DESCRIPTION OF SPECIFIC EMBODIMENTS

Figure 1:
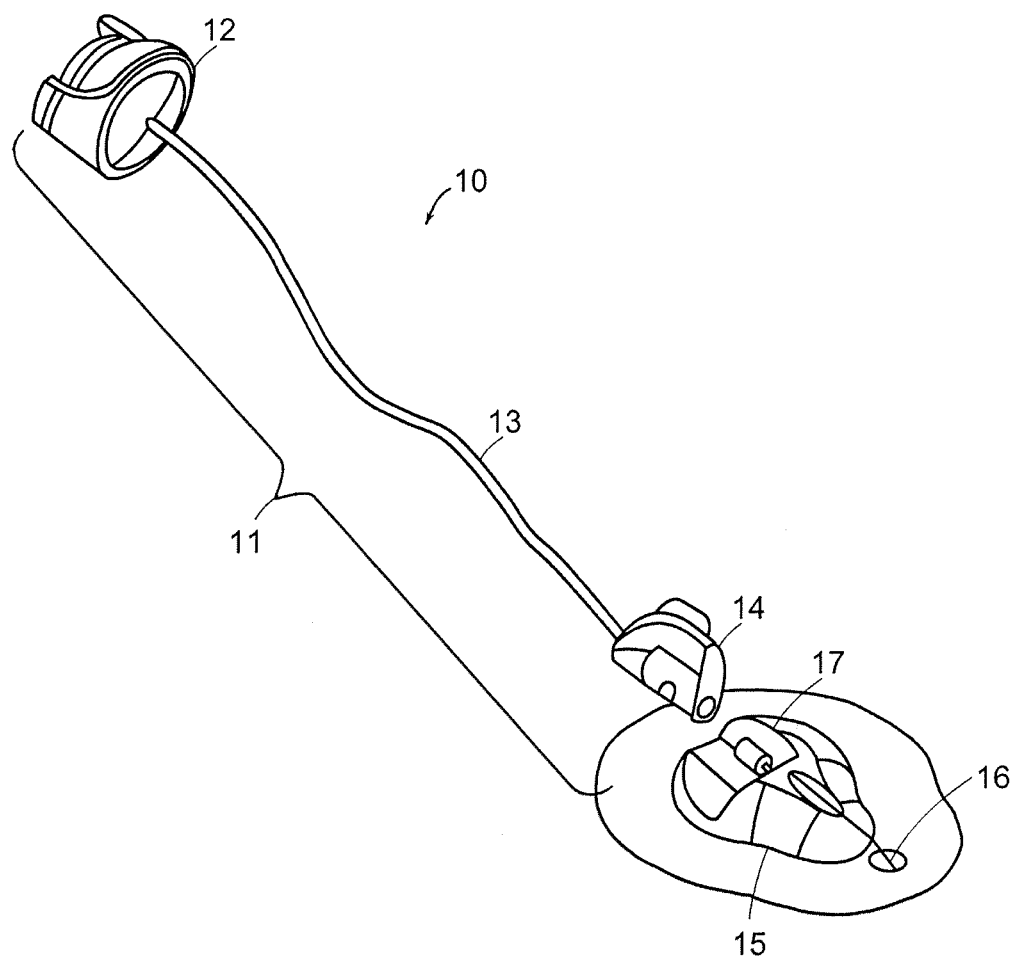
FIG. 1 is a perspective view of an infusion set 10 for delivery of a fluid to a patient, in accordance with one embodiment of the present invention.

FIG. 1 is an overall view of an infusion set 10, in accordance with one embodiment of the invention, for delivery of a fluid to a patient. It may also be used to deliver fluid from a fluid delivery device to a porous medium. In the description, an infusion pump will serve as an example of a fluid delivery device and a human tissue will serve as an example of a porous medium. Fluid may be, for example, a drug, such as insulin. Like numbers in successive figures refer to the same or similar items.

The infusion set 10 includes a tubing set 11. The tubing set 11 includes tubing 13 that is attached at one end to a hub 12. The hub 12 serves as an interface between the tubing 13 and a pump assembly (not shown). Attached to the other end of the tubing set 11 is an infusion flap 14 that interfaces with a cannula assembly 15.

The cannula assembly 15 includes a cannula body 17. Attached to the cannula body 17 is a cannula 16, for subcutaneous insertion into the patient. The cannula 16 may be made of steel or alternatively, a soft and/or flexible material to help prevent patient discomfort, such as Teflon or other plastic. The cannula 16 may protrude from the bottom or side of the cannula body 17 at various angles. For example, without limitation, the cannula 16 may protrude from the front edge of the cannula body 17 at a shallow angle of 15-30 degrees. As another example, the cannula 16 may form a 90 degree angle with the bottom of the cannula body 17. Further detail of the cannula assembly 15 is provided in subsequent drawings including FIG. 2.

Within the cannula body 17 is a passageway adapted to receive the proximal or upstream end of the cannula 16. The passageway includes at least one self-sealing septum that can be penetrated, for example, by an infusion or insertion needle.

Figure 2:
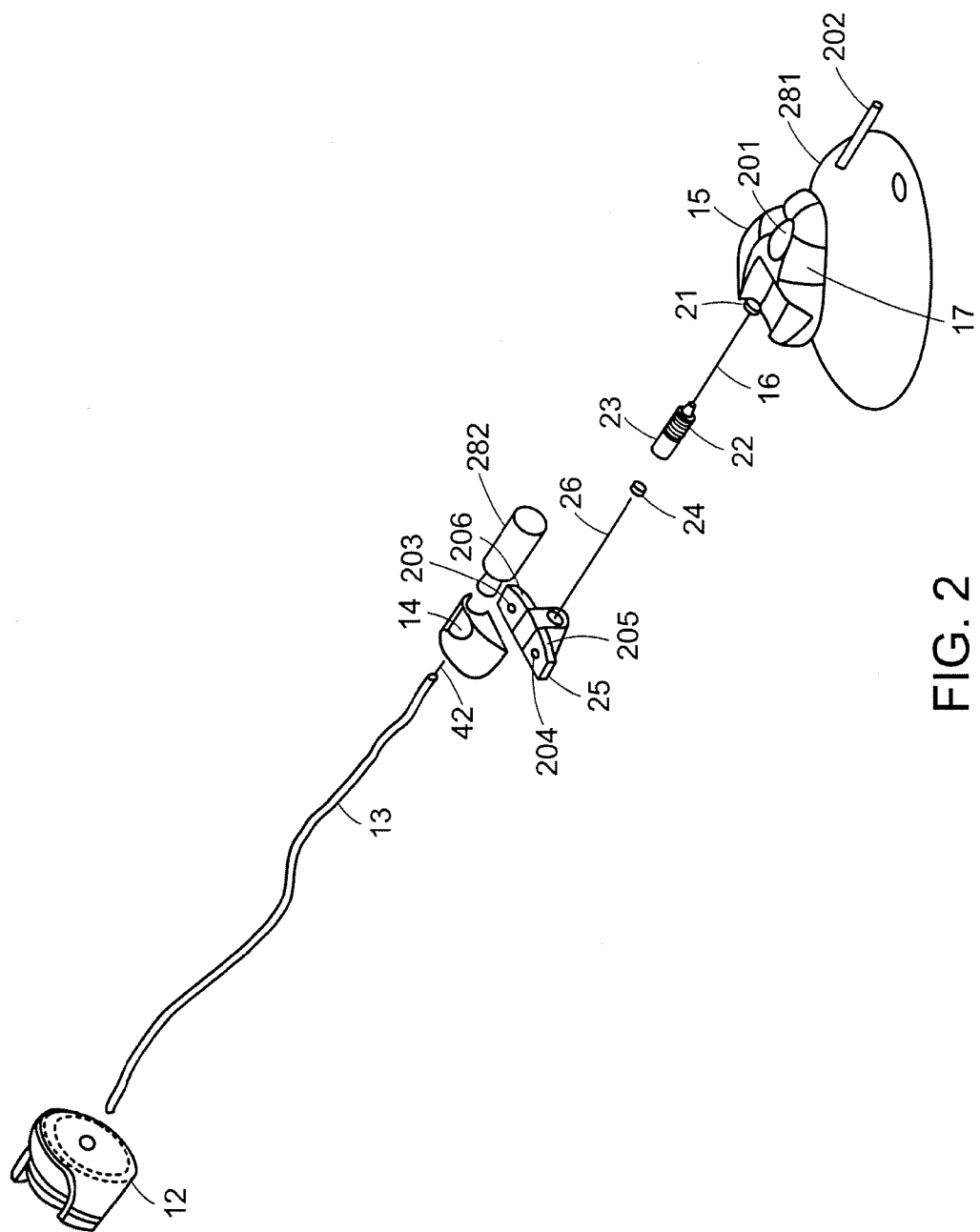
FIG. 2 is a further breakdown of the infusion set shown in FIG. 1, in accordance with one embodiment of the present invention.

FIG. 2 is a further breakdown of parts in the infusion set shown in FIG. 1. The cannula assembly may be fabricated, in accordance with one embodiment of the invention, by inserting the cannula 16 through a hole in a cannula locking ring 21. The cannula locking ring 21 is then attached to a core insert 22 by a snap fit mechanism, ultrasonic welding, or other means known in the art. The proximal end of the cannula 16 is flared, such that it is captured and held in place between the core insert 22 and the locking ring 21. Both the cannula locking ring 21 and core insert 22 may be made of plastic or other suitable material.

The core insert 22 defines a passageway having a first end and a second end. The first end receives the proximal end of the cannula 16, as described above. The second end of the core insert 22 acts as septum housing 23. A self-sealing septum 24 is inserted into the open end of the septum housing 23, which is then ultrasonically flared to capture the septum 24 inside the core insert 22. The core insert 22 and locking ring 21 are then overmolded to form a soft body 17 for user comfort.

The body 17 of the cannula assembly is typically a compact and low profile component. When seen from the top, the cannula body 17 may be, for example, circular, elliptical or triangular in shape and/or advantageously elongated for easy patient handling. All or a portion 201 of the body 17 may be made clear or transparent to facilitate viewing of the core insert 22 and/or infusion site.

The cannula 16 may be inserted subcutaneously with the aid of an insertion flap 25. The insertion flap 25 includes an insertion needle 26, typically made of steel, that assists the cannula 16 in penetrating the skin. After inserting the cannula 16, the insertion flap 25 is removed, and the infusion flap 14 is removably attached to the cannula assembly 15 for delivery of fluid to the patient.

Figure 3:
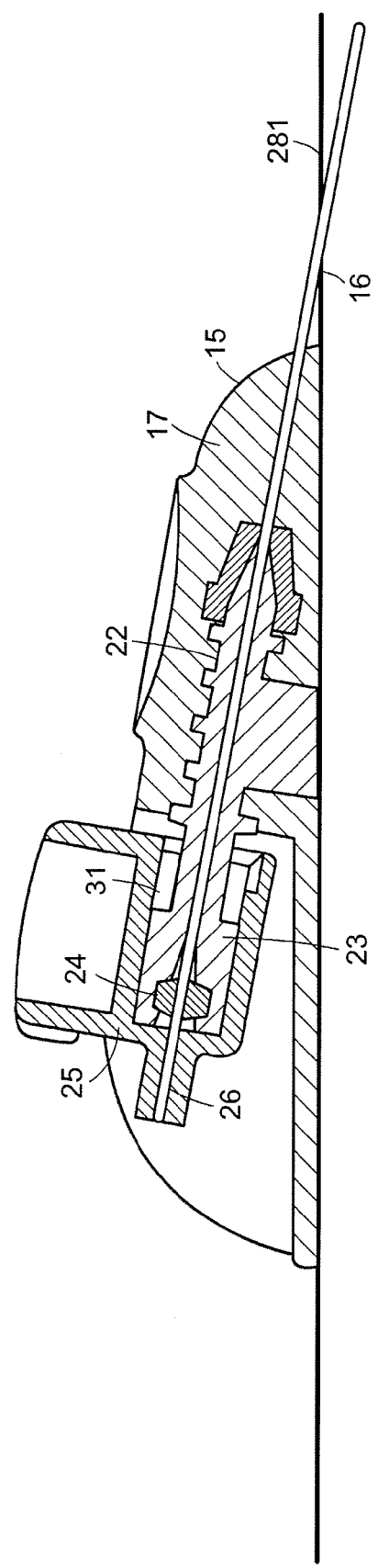
FIG. 3 is a cross-sectional view of a cannula assembly with an insertion flap attached (and locked), in accordance with one embodiment of the present invention.

In accordance with one embodiment of the invention, FIG. 3 shows a cross-sectional view of the cannula assembly 15 with the insertion flap 25 attached. The insertion flap 25 supports a proximal end of the insertion needle 26 which protrudes from the flap 25 and terminates in a sharp distal end. When the insertion flap 25 is not in use and is removed from the cannula assembly 15, the sharp end of the insertion needle 26 may be covered by a needle guard 202 (shown in FIG. 2), which prevents accidental contact with the needle 26.

The proximal end of the insertion needle 26 is seated within a cylindrical shaped open ended (female) connector 31 that slides onto and mates with the male septum housing 23 of the cannula assembly 15. The distal end of the insertion needle 26 is inserted through the self-sealing septum 24, through the core insert 22, and into the cannula 16. When the insertion flap 25 and septum housing 23 are fully mated, the sharp tip of the insertion needle 26 may extend slightly beyond the distal end tip of the cannula 16. The insertion flap may interface with an auto-insertion device (not shown) that can be used, for example, by a patient lacking the dexterity or strength to subcutaneously insert the cannula 16 by him or her self. To interface with the auto-insertion device, the insertion flap 25 may include, for example, a flat top with a pair of wings 205 and 206 and mounting holes 203 and 204 for attaching the auto-insertion device (see FIG. 2). When manually inserting the cannula 16, the patient grasps the attached insertion flap 25 and/or cannula body 17 and pushes the cannula 16, with the insertion needle 26 inserted, into the infusion site. The infusion site may be prepped prior to insertion of the cannula 16 with a sterilizing fluid or by placement of a mounting patch onto the patient's skin, as known in the art. After the cannula 16 has been inserted into the patient, the insertion flap 25 and needle 26 is withdrawn from the cannula assembly 15. The cannula assembly 15 can then be secured to the patient by peeling a cover off an adhesive strip coupled to the bottom of the cannula body 17, and pressing the adhesive 281 against the patient's skin or mounting patch.

Figure 4:
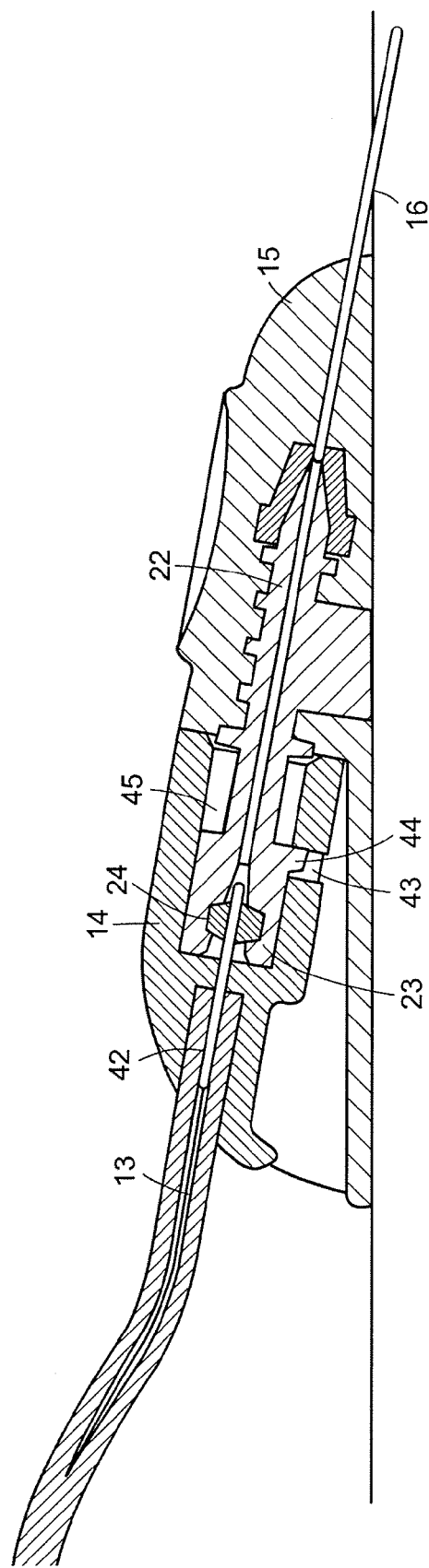
FIG. 4 is a cross-sectional view of an infusion flap mated (and locked) to a cannula assembly, in accordance with one embodiment of the present invention.

Referring back to FIGS. 1 and 2, upon securing the cannula assembly 15 to the patient, the infusion flap 14 is attached to the cannula assembly 15 permitting fluid communication between the tubing set 11 and the cannula 16. The infusion flap 14 may attach to the top or one of sides of the cannula assembly 15. In accordance with one embodiment of the invention, FIG. 4 is a cross-sectional view of the infusion flap 14 mated (and locked) to the cannula assembly 15. The infusion flap 14 includes an infusion needle 42 attached to the inside of the tubing 13, by, for example, a suitable adhesive. In various embodiments, the tubing may be microbore tubing.

The proximal end of the infusion needle 42 is seated within a generally cylindrically shaped, open ended, female connector 45 on the infusion flap 14 that slides onto and mates with the male septum housing 23 of the cannula assembly 15. The sharp, distal end of the infusion needle 42 typically does not extend beyond the open end of the female connector 45, preventing inadvertent needle sticks and/or damage to the needle. When the infusion flap 14 is mated to the cannula assembly 15, the infusion needle penetrates the septum 24, allowing fluid in the tubing 13 to flow through the cannula 16. The length of the infusion needle 42 is such that it does not protrude into, and damage the cannula 16.

Figure 5:
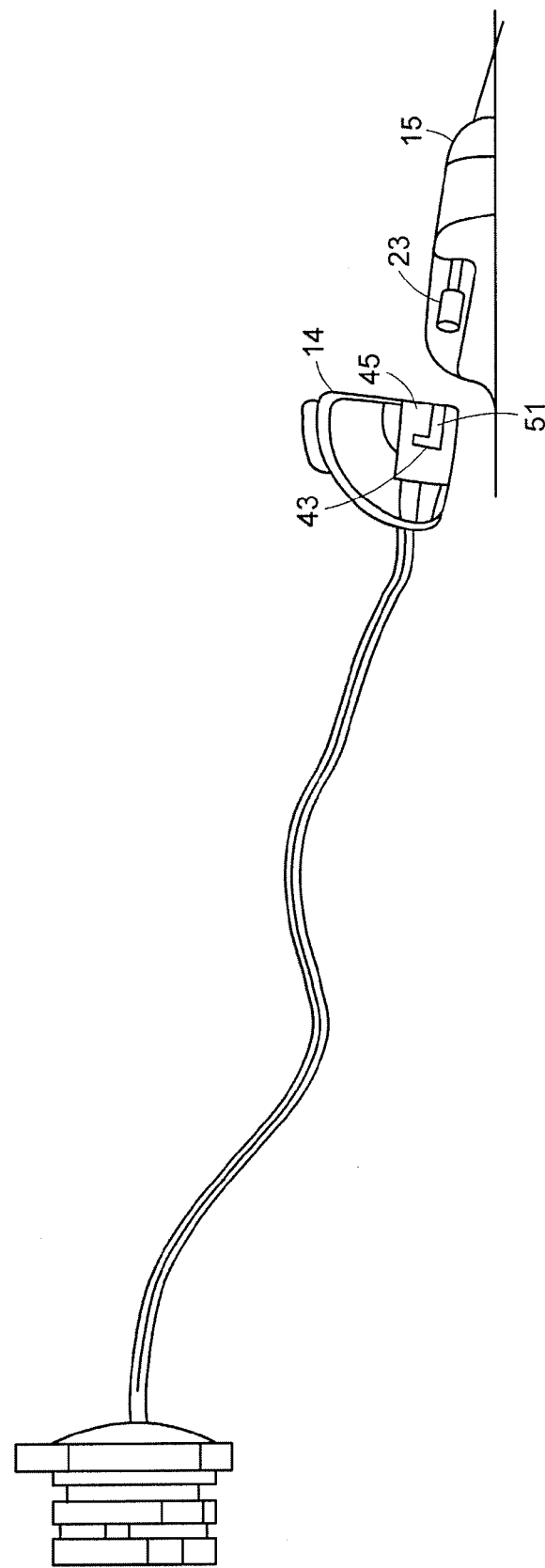
FIG. 5 is a side view of the embodiment of FIG. 4 with the infusion flap in position for mating with the cannula assembly.

So as to prevent inadvertent separation of the infusion flap 14 and the cannula assembly 15, a locking mechanism may be provided. The locking mechanism may include, without limitation, a locking receptacle 43 on the female connector 45 of the infusion flap 14 that engages a locking lug 44 on the core insert 22 of the cannula assembly. The locking lug 44 may be disposed on the septum housing 23, for example. FIG. 5 is a side view showing the infusion flap 14 in position for mating with the cannula assembly 15. To slide the male septum housing 23 into the female connector 45, an opening slot 51 of the receptacle 43 is aligned with the locking lug 44. When fully inserted, the base wall of the female connector 45 may abut the distal end of the male septum housing 23, and/or the distal end of the infusion flap 14 may make contact with the body of the cannula assembly 15, such that the infusion needle pierces the septum contained within the septum housing.

Figure 6:
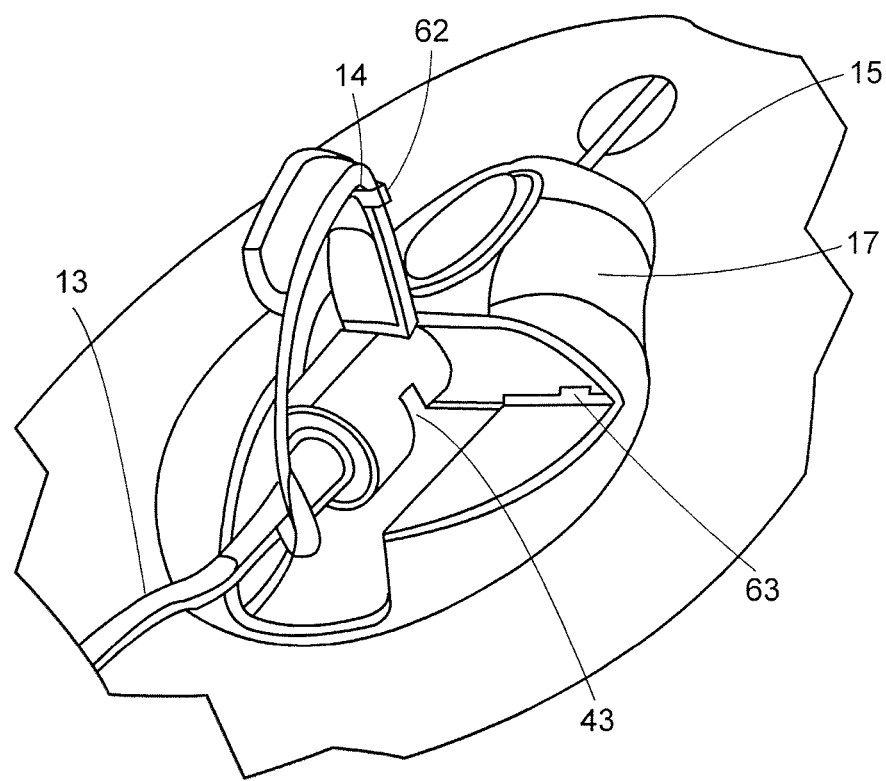
FIG. 6 is a perspective view of the embodiment of FIG. 4 with the infusion flap mated to the cannula assembly.

FIG. 6 is a detailed perspective view showing the infusion flap 14 when mated to the cannula assembly 15. To lock the infusion flap 14 onto the cannula assembly 15, the locking lug 44 (shown in FIG. 4) is engaged with the lug receptacle 43 by rotating the infusion flap 14 clockwise. The locking lug 44 (shown in FIG. 4) prevents the infusion flap 14 from disconnecting with the cannula assembly 15 when a longitudinal force is applied, such as when the tubing 13 is pulled on. In various embodiments, the infusion flap 14 may also include a snap fit mechanism to prevent the infusion flap 14 from inadvertently rotating open. The snap fit mechanism may include, without limitation, a detent 62 that, when the infusion flap 14 is rotated clockwise, fits into a notch 63 in the cannula body 17.

Figure 7:
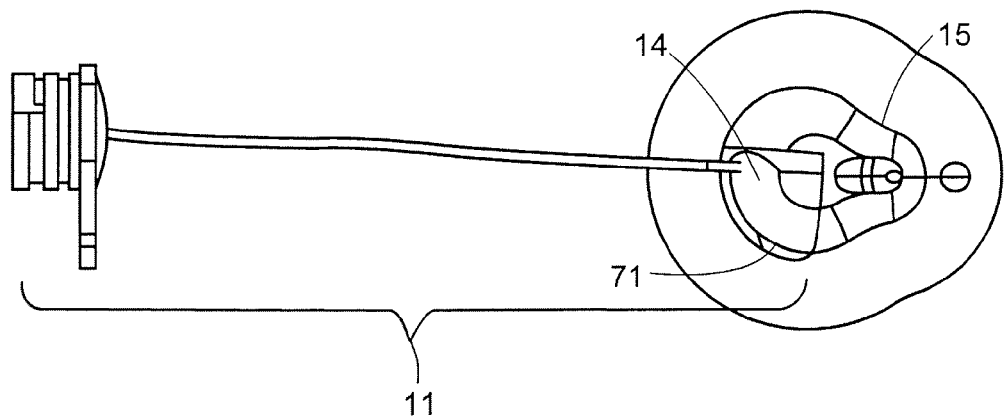
FIG. 7 is a top view of the embodiment of FIG. 4 with the tubing set locked to the cannula assembly.
Figure 8:
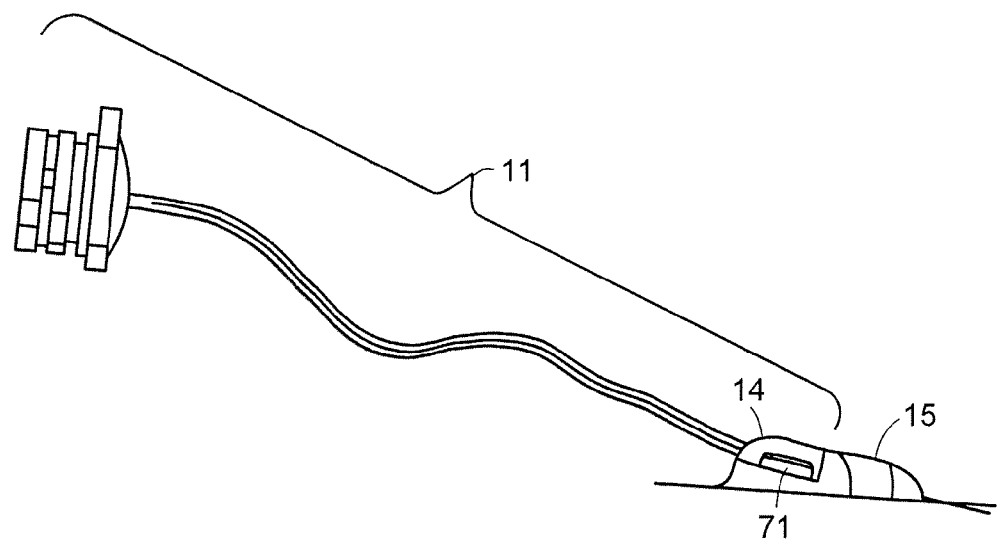
FIG. 8 is a side view of the embodiment of FIG. 4 with the tubing set locked to the cannula assembly.

FIGS. 7 and 8 show a top view and side view of the tubing set 11 locked to the cannula assembly. The infusion flap 14 can be easily removed from the cannula assembly 15 by lifting up on a lift tab 71 on the infusion flap 14 and rotating the infusion flap 14 counter-clockwise so as to align the slot 51 (shown in FIG. 4) with the locking lug 44 (shown in FIG. 4). The infusion flap 14 is then pulled apart from the cannula assembly 15 and the septum 24 (shown in FIG. 4) self-seals.

Figure 9:
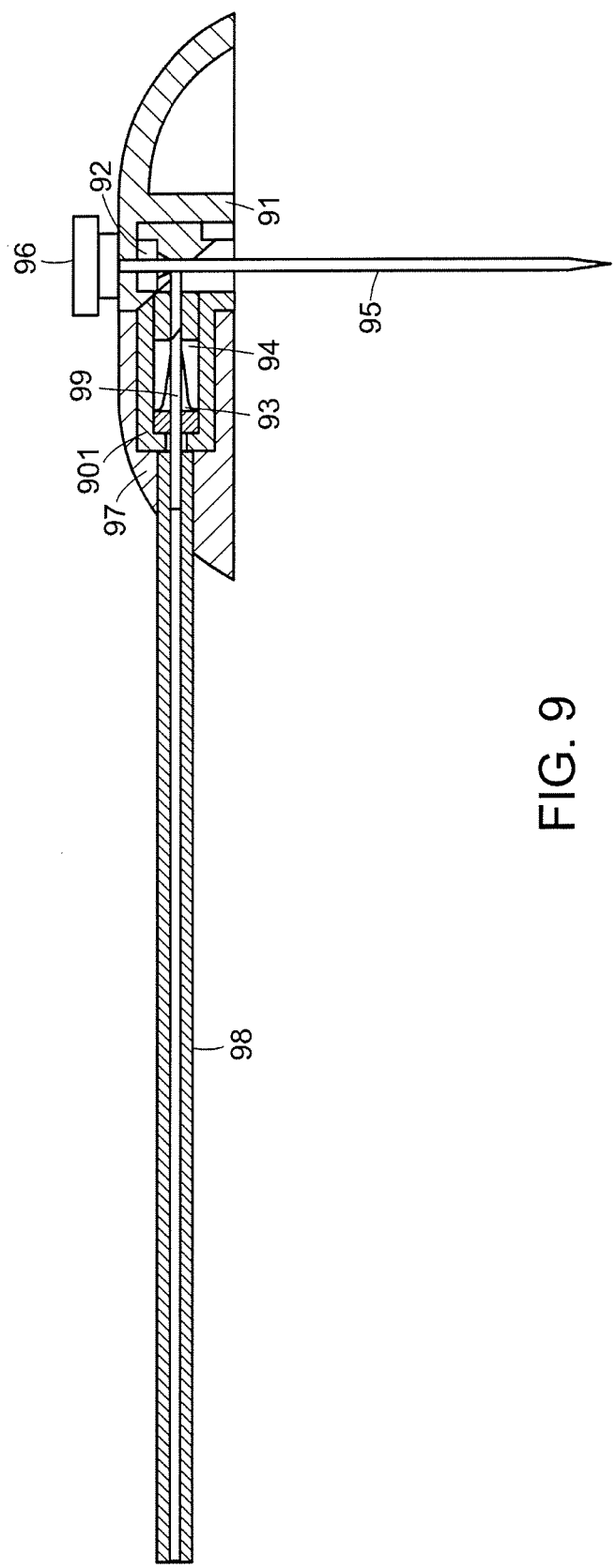
FIG. 9 is a cross-sectional view of an infusion flap mated (and locked) to a cannula assembly that includes a first septum and a second septum contained with a septum housing, in accordance with one embodiment of the present invention.

In accordance with another embodiment of the invention, FIG. 9 shows a cross-sectional view of an infusion flap 97 attached to a cannula assembly 91 that includes a first septum 92 and a second septum 93 contained with a septum housing 94. The septum housing 94 defines a passageway that is coupled to a cannula 95. The first septum 92 is advantageously located for penetration by an insertion needle 96, while the second septum is positioned for penetration by an infusion needle 99. To subcutaneously insert the cannula 95, the insertion needle 96 is inserted through the first septum 92 and into the cannula 95. After cannula 95 insertion, the insertion needle 96 is removed and the first septum 92 self-seals to prevent fluid leakage. The cannula assembly 91 attaches to the user's body or mounting patch with an adhesive.

As in previous embodiments, tubing 98 is coupled at a first end to the infusion flap 97, and to a hub (not shown) that interfaces with a pump assembly at a second end. An infusion needle 99 is attached to the inside of the tubing 98 at the first end and is seated within a generally cylindrically shaped, open ended, female connector 901 on the infusion flap 97. When the infusion flap 97 is mated to the cannula assembly 91, the connector 901 slides onto and mates with the male septum housing 94, such that the infusion needle 99 pierces the second septum 93 allowing fluid in the tubing 98 to flow to the cannula 95.

Figure 10:
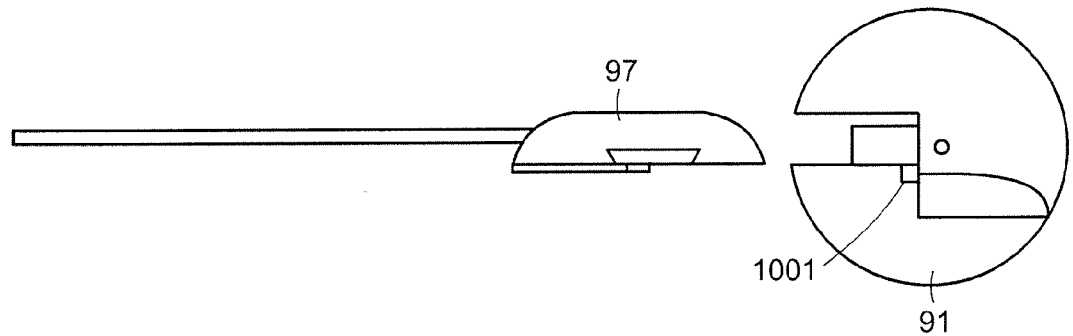
FIG. 10 is a top view of the embodiment of FIG. 9 with the infusion flap in position for mating with the cannula assembly.
Figure 11:
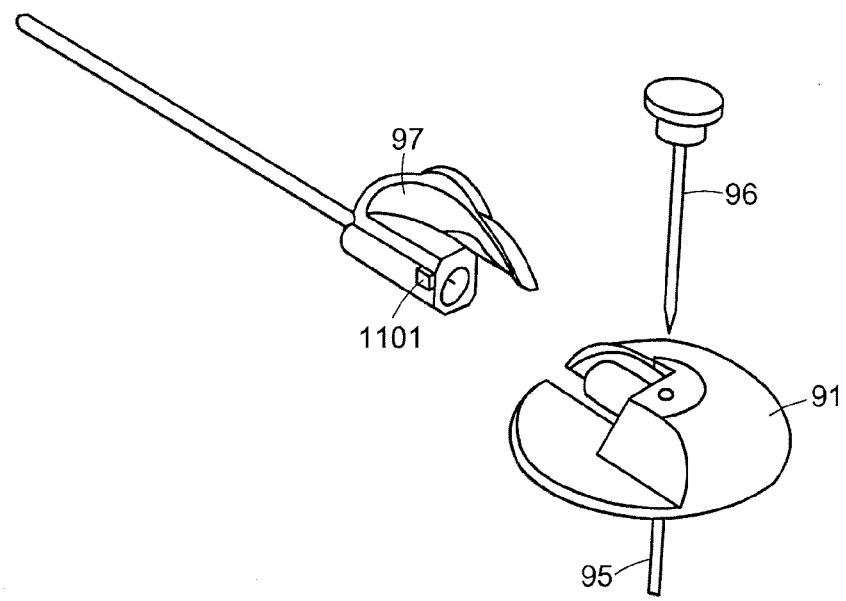
FIG. 11 is a side view of the embodiment of FIG. 9 with the infusion flap in position for mating with the cannula assembly.
Figure 12:
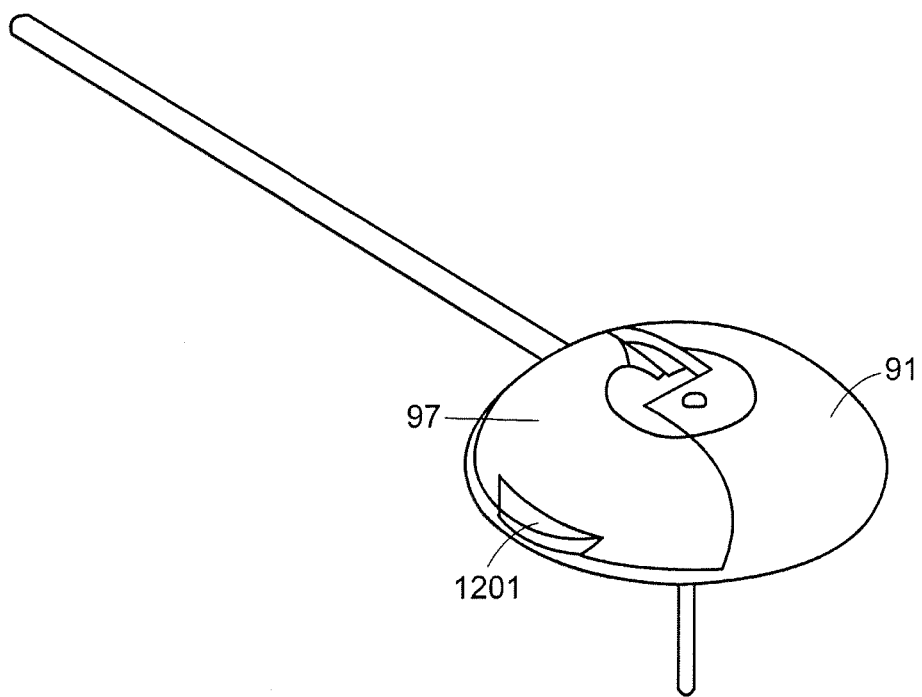
FIG. 12 is a perspective view of the embodiment of FIG. 9 with the infusion flap mated to the cannula assembly.

FIGS. 10 and 11 are a top view and a side view of the infusion flap 97 in position for mating with the cannula assembly 91. The insertion needle 96 has been removed. To prevent inadvertent separation of the infusion flap 97 and the cannula assembly 91, a locking mechanism for securing the infusion flap 97 to the cannula assembly 91 may be provided. For example, the cannula assembly 91 may include a lug receptacle 1001 (see FIG. 10) that engages with a locking lug 1101 (see FIG. 11) on the infusion flap 97. To lock the infusion flap 97 to the cannula assembly 91, the locking lug is engaged with the lug receptacle 1001 by rotating the infusion flap clockwise. Engagement in this fashion prevents disconnection of the tubing when pulled on. FIG. 12 shows the infusion flap 97 mated and locked onto the cannula assembly 91.

To remove the infusion flap 97 from the cannula assembly 91, one lifts up on a lift tab 1201 and rotates the infusion flap 97 counter-clockwise. The infusion flap 97 is then pulled apart from the cannula assembly 91 and the second septum 93 (see FIG. 9) self-heals.

Figure 13:
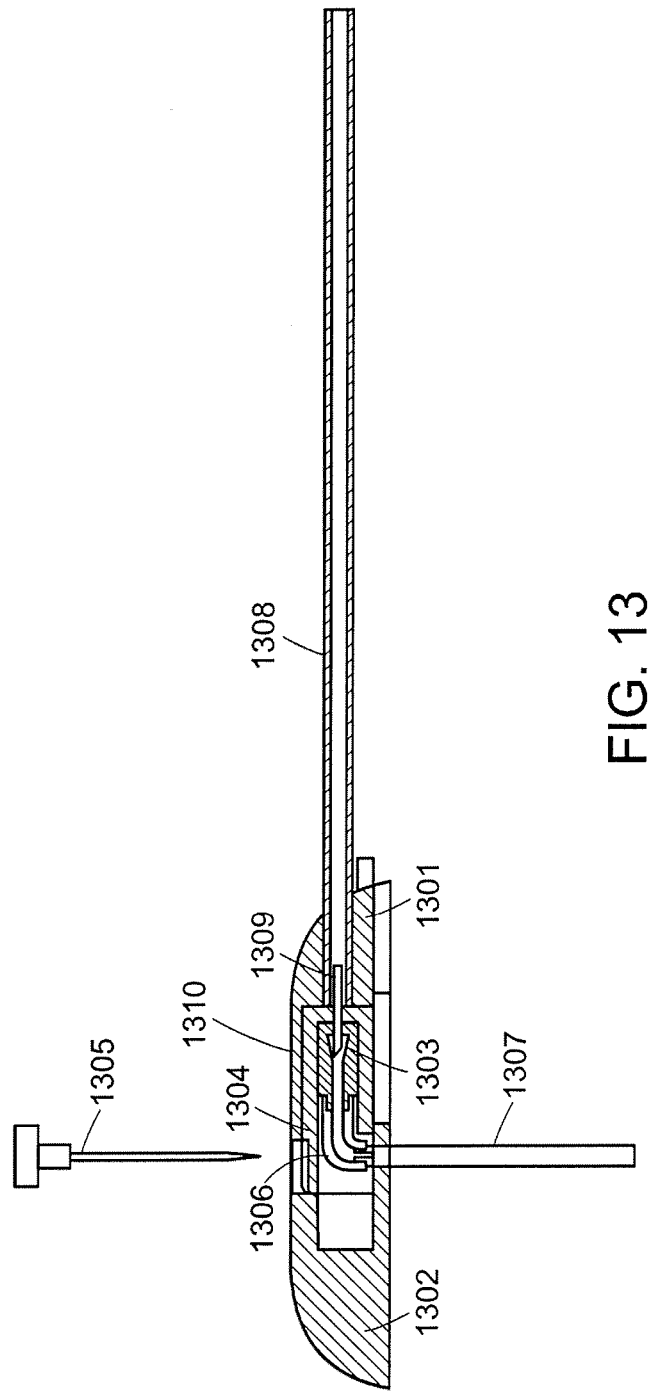
FIG. 13 is a cross-sectional view of an infusion flap mated (and latched) to a cannula assembly, wherein the cannula assembly includes a single septum located in a rotatable septum housing, in accordance with one embodiment of the present invention.

In accordance with another embodiment of the invention, FIG. 13 is a cross-sectional view of an infusion flap 1301 attached to a cannula assembly 1302, wherein the cannula assembly 1302 includes a single septum 1303 located in a rotatable septum housing 1304. A single septum 1303 and rotatable septum housing 1304 advantageously prevents leakage problems inherent in dual septum designs, while still permitting the septum housing 1304 to be positioned, for example, vertically for insertion of an insertion needle 1305, or horizontally after mating with the infusion flap 1301.

The septum housing 1304 is rotatably attached to the cannula assembly by, for example, a pivot or hinge mechanism. Attached to the septum housing 1304 and/or septum 1303 is a first end of a flexible tube 1306, which is further attached at a second end to a proximal end of a cannula 1307 mounted within the cannula assembly 1302. The flexible tubing 1306 may be attached to the septum housing 1304 and/or cannula assembly 1302 using, without limitation, a suitable adhesive.

Tubing 1308 is coupled at a first end to the infusion flap 1301, and to a hub (not shown) that interfaces with a pump assembly at a second end. An infusion needle 1309 is attached to the inside of the tubing 1308 at the first end and is seated within an open ended, female connector 1310 on the infusion flap 1301. The connector 1310 and male septum housing 1304 may be of variable shape, such as, for example, a cylindrical, rectangular, or square shape. When the infusion flap 1301 is mated to the cannula assembly 1302, the connector 1310 slides onto and mates with the male septum housing 1304, such that the infusion needle 1309 pierces the septum 1303 allowing fluid in the tubing 1308 to flow to the cannula 1307. In various embodiments, the infusion needle 1305 is slightly larger than the insertion needle 1305, so as to seal the hole previously created by the insertion needle 1305.

Figure 15:
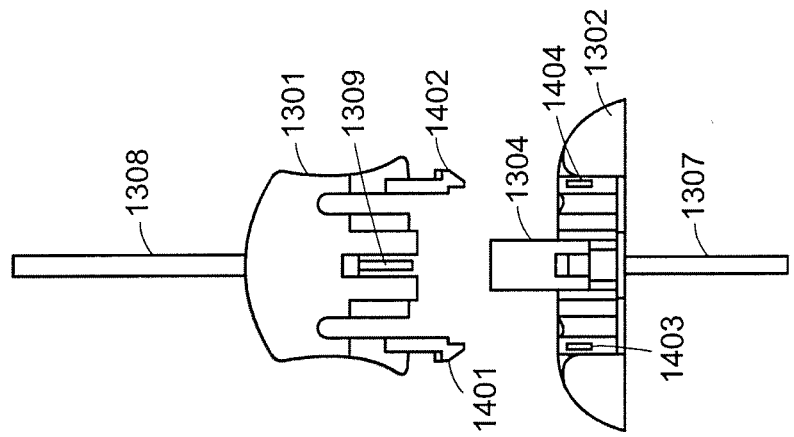
FIG. 15 is a side view of the embodiment of FIG. 13 with the infusion flap in position for mating with the cannula assembly.
Figure 14:
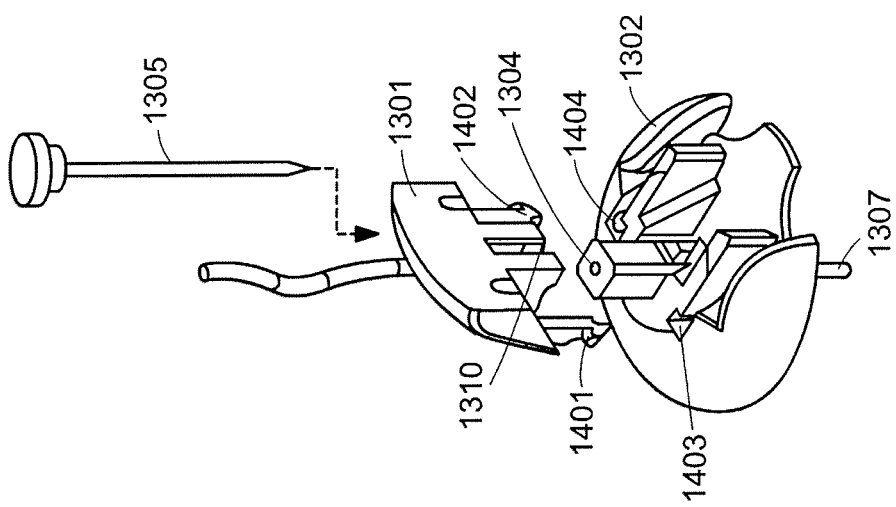
FIG. 14 is a perspective view of the embodiment of FIG. 13 with the infusion flap in position for mating with a cannula assembly.
Figure 17:
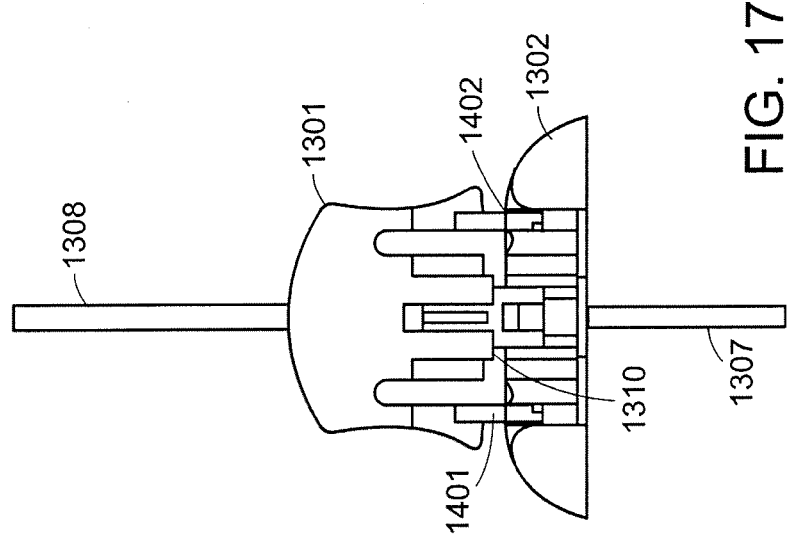
FIG. 17 is a side view of the embodiment of FIG. 13 with the infusion flap mated and latched onto the cannula assembly.
Figure 16:
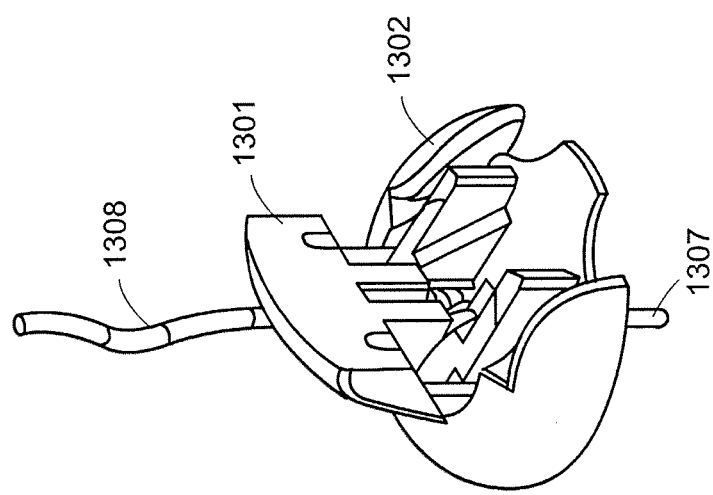
FIG. 16 is a perspective view of the embodiment of FIG. 13 with the infusion flap mated and latched onto the cannula assembly.
Figure 18:
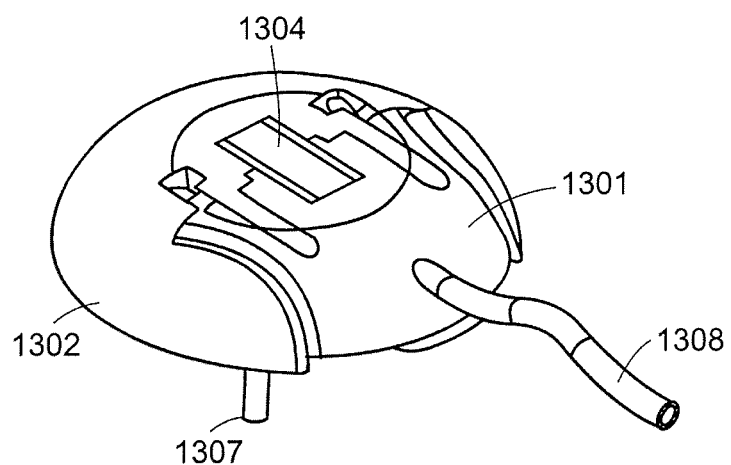
FIG. 18 is a perspective view of embodiment of FIG. 13, with the infusion flap latched to the septum housing and the septum housing rotated 90 degrees.

The infusion flap 1301 is easily connected and disconnected to the cannula assembly 1302. FIGS. 14 and 15 show a perspective view and a side view, respectively, of the infusion flap 1301 in position for mating with the cannula assembly 1302. The septum housing 1304 has been rotated such that it is perpendicular to the longitudinal axis of the cannula assembly 1302, so as to allow for insertion of the infusion flap 1301. The insertion needle 1305 has been removed. To prevent inadvertent separation of the infusion flap 1301 and the cannula assembly 1302, a locking mechanism may be provided. The locking mechanism may include, for example, locking tangs 1401 and 1402 on the infusion flap 1301 which engage with tang receptacles 1403 and 1404 located on the cannula assembly 1302 when the infusion flap 1301 is pushed onto the cannula assembly 1302. FIGS. 16 and 17 show a perspective view and a side view, respectively, of the infusion flap 1301 mated and latched onto the cannula assembly 1302. At this point, the infusion needle 1309 penetrates the septum 1303 in the septum housing 1304 (see FIG. 13). Upon being mated and latched onto the cannula assembly 1302, the infusion flap 1301 and septum housing 1304 may be rotated 90 degrees, such that the infusion flap lays flat against the cannula assembly 1302, as shown in FIG. 18. A detent (not shown) may latch the infusion flap 1301 to the cannula assembly 1302 with a snap action. The flexible tube 1306 bends as the septum housing 1304 rotates, providing a leak tight fluid path between the tubing 1308 and the cannula 1307.

To remove the infusion flap 1301 from the cannula assembly 1302, one lifts up on, and rotates the infusion flap 1301 90 degrees so that the septum housing 1304 is once again perpendicular to the longitudinal axis of the cannula assembly 1302. The infusion flap 1301 is then disengaged by pinching the locking tangs 1401 and 1402 towards each other, and pulling the infusion flap 1301 away from the cannula assembly 1302.

Figure 19:
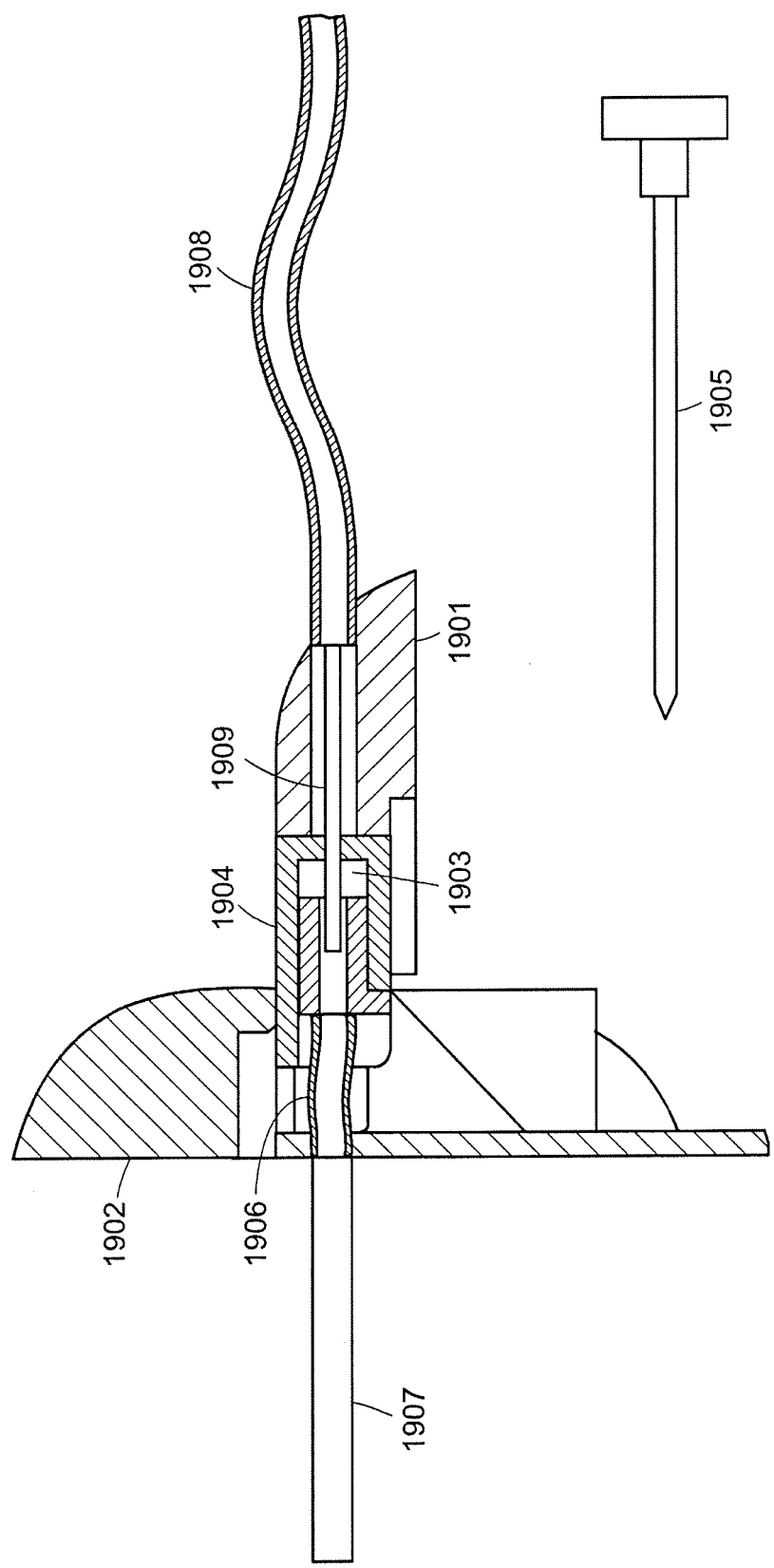
FIG. 19 is a cross-sectional view of an infusion flap that includes a single septum located in a rotatable septum housing, in accordance with one embodiment of the invention.

In accordance with another embodiment of the invention, FIG. 19 is a cross-sectional view of an infusion flap 1901 attached to a cannula assembly 1902 that, similar to the above described embodiment, includes a single septum 1903 located in a rotatable septum housing 1904, but which has an alternative locking mechanism. FIG. 19 shows the infusion flap 1901 and the cannula assembly 1902 in a mated position, just prior to being latched. The insertion needle has been removed 1905.

Figure 20:
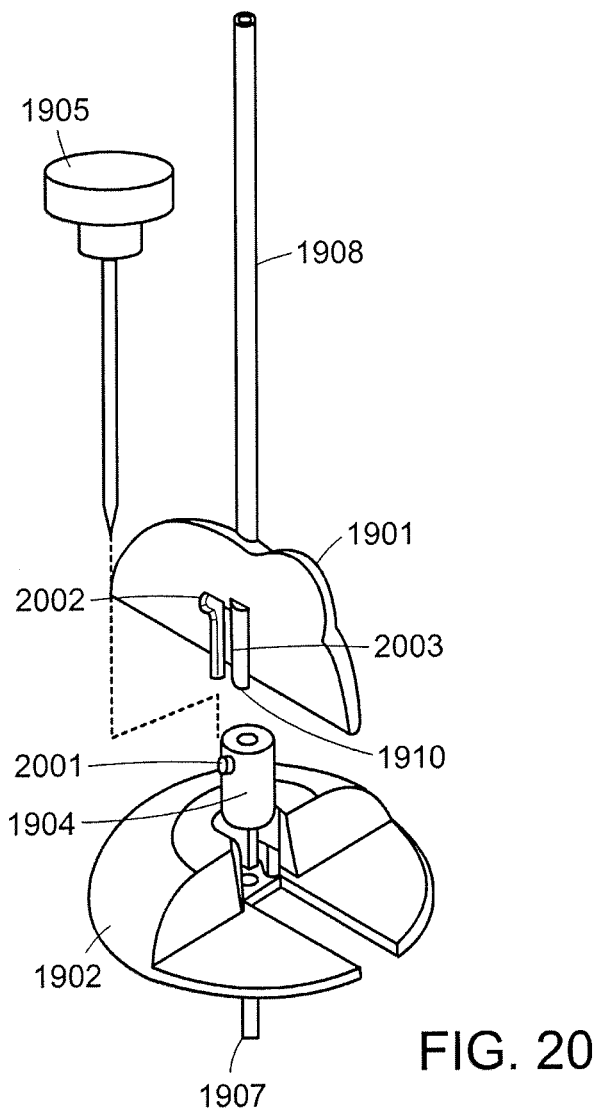
FIG. 20 is a perspective view of the embodiment of FIG. 19 with the infusion flap in position for mating with the cannula assembly.
Figure 21:
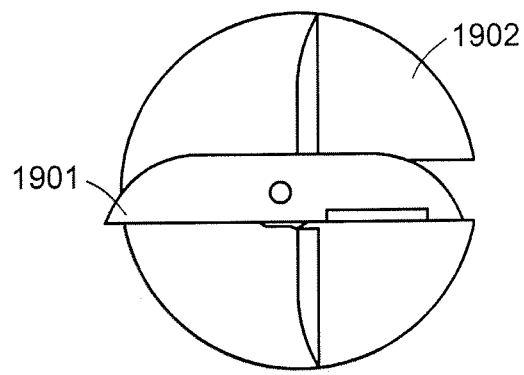
FIG. 21 is a top view of the embodiment of FIG. 19 with the infusion flap in position for mating with the cannula assembly.
Figure 22:
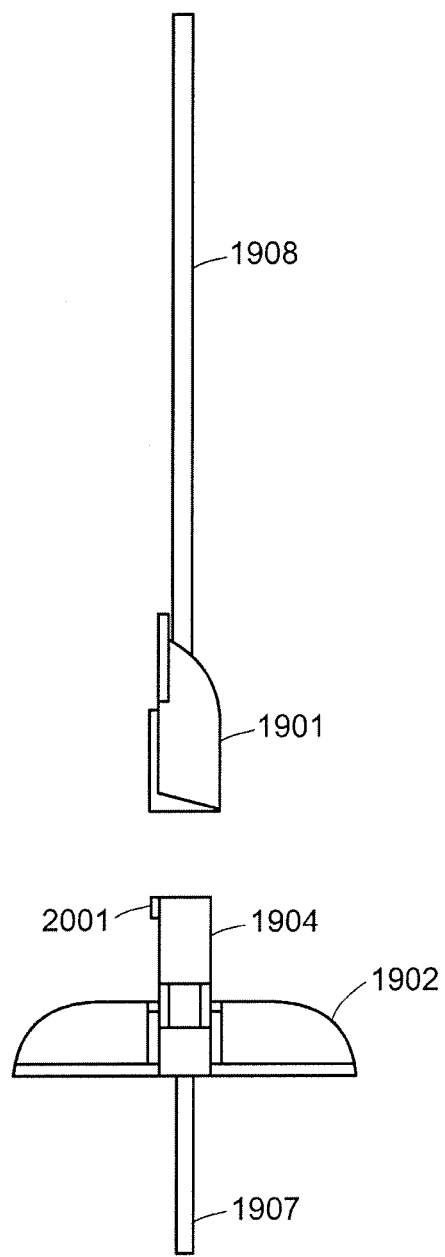
FIG. 22 is a side view of the embodiment of FIG. 19 with the infusion flap in position for mating with the cannula assembly.
Figure 24:
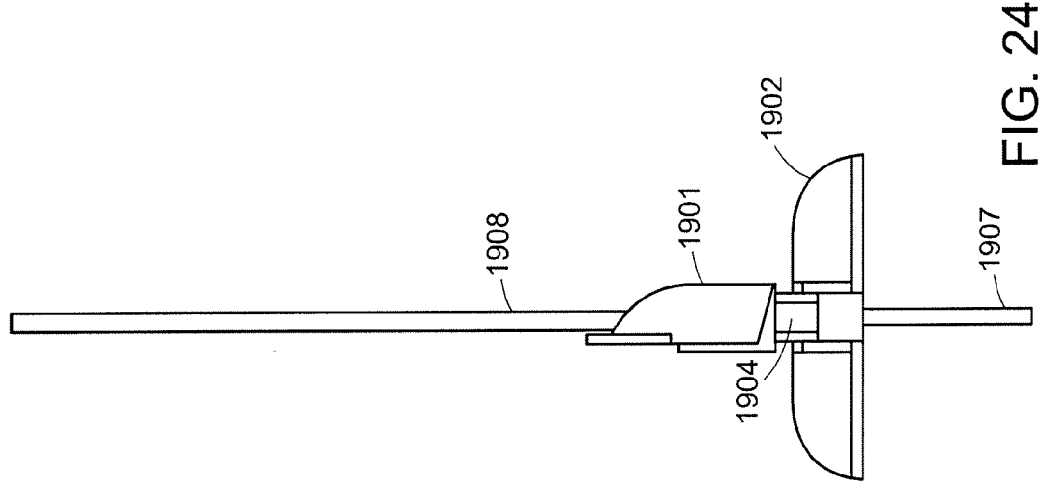
FIG. 24 is a side view of the embodiment of FIG. 19 with the infusion flap mated with the cannula assembly 1902.
Figure 23:
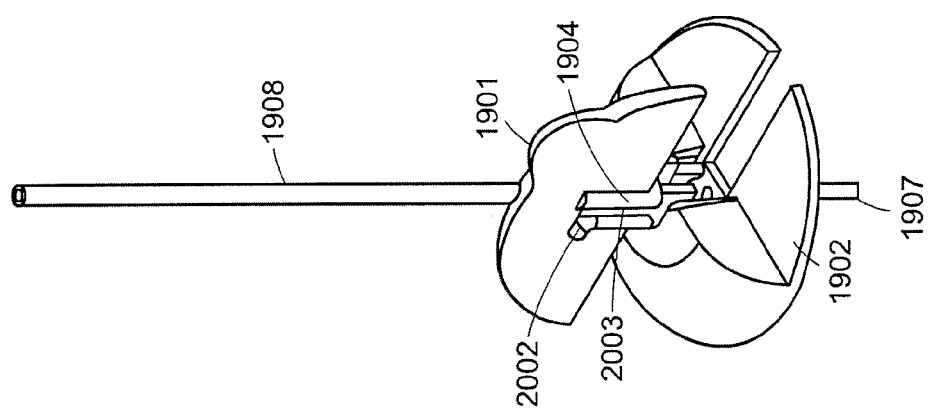
FIG. 23 is a perspective view of the embodiment of FIG. 19 with the infusion flap mated with the cannula assembly 1902.

The open ended female connector 1910 (see FIG. 20) on the infusion flap 1901, which seats the infusion needle 1909, is generally cylindrical shaped, such that the connector can be slid onto and mated with the male septum housing 1904. FIGS. 20, 21, and 22 show a perspective view, a top view and a side view, respectively, of the infusion flap 1901 in position for mating with the cannula assembly 1902. The male septum housing 1904 includes a locking lug 2001 which mates with a lug receptacle 2002 on the connector 1910. The user aligns receptacle slot 2003 on the female connector 1910 with the locking lug 2001, such that the female connector 1910 can be slid onto, and mated with, the male septum housing 1904. FIGS. 23 and 24 show a perspective view and a side view, respectively, of the infusion flap 1901 mated with the cannula assembly 1902. At this point, the infusion needle 1909 pierces the septum 1903 (see FIG. 19).

Figure 26:
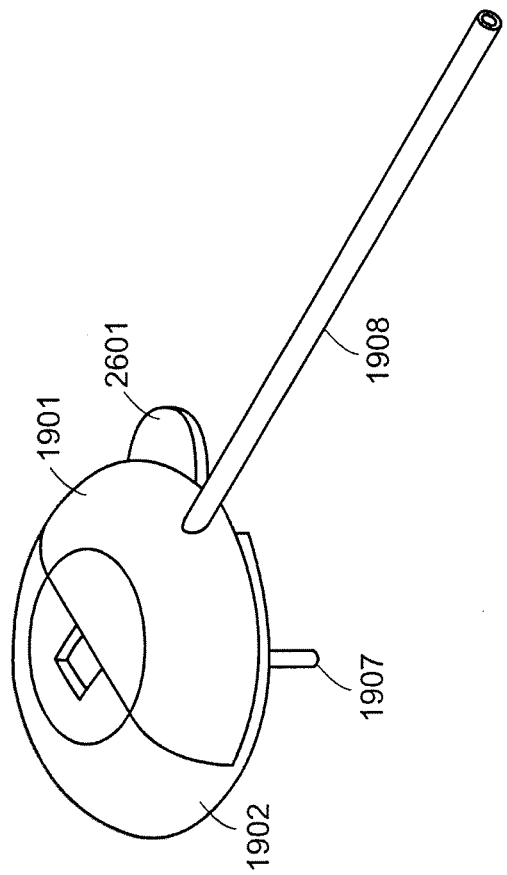
FIG. 26 is a perspective view of the embodiment of FIG. 19 after the locking lug is engaged with the lug receptacle and the septum housing 1904 is rotated.
Figure 25:
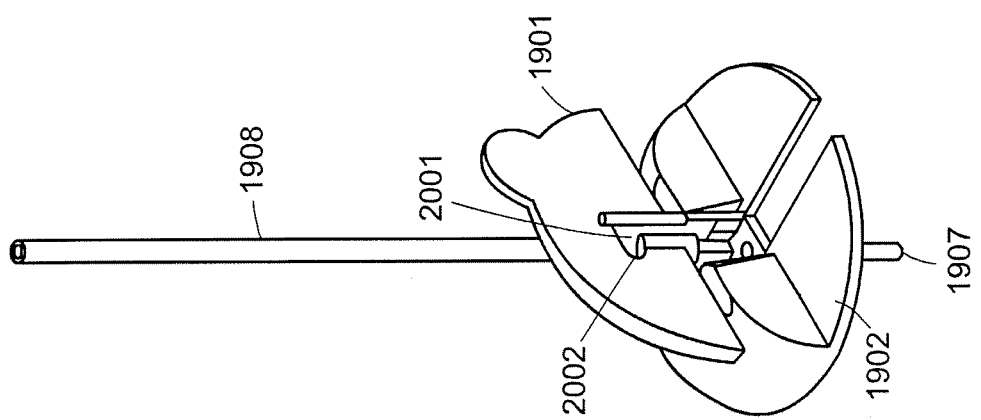
FIG. 25 is a perspective view of the embodiment of FIG. 19 with the locking lug engaged with the lug receptacle by rotating the infusion flap 25.

The locking lug 2001 is then engaged with the lug receptacle 2002 by rotating the infusion flap 25 counterclockwise (or clockwise depending on the location of the lug recepticle), as shown in FIG. 25. After engagement, the infusion flap 1901 and septum housing 1904 can be rotated 90 degrees, such that the infusion flap 1901 lays flat against the cannula assembly 1902, as shown in FIG. 26. A detent (not shown) may latch the infusion flap 1901 to the cannula assembly 1902 with a snap action. The flexible tube 1906 bends as the septum housing 1904 rotates, providing a leak tight fluid path between the tubing 1908 and the cannula 1907.

To remove the infusion flap 1901 from the cannula assembly 1902, one lifts up on a lift tab 2601 on the infusion flap 1901 and rotates the infusion flap 1901 90 degrees so that the septum housing 1904 is perpendicular to the longitudinal axis of the cannula assembly 1902. The infusion flap 1901 is then disengaged by rotating the infusion flap 90 degrees clockwise, and pulling the infusion flap 1901 away from the cannula assembly 1902.

Referring back to FIG. 1, the tubing 13 attaches at one end to a hub 12 for interfacing and receiving a fluid from a fluid delivery device (not shown). The fluid may be a drug, such as insulin. The fluid delivery device may be, without limitation, an infusion pump assembly.

The hub 12 may be of various shapes. For example, the hub 12 may be asymmetric, circular, or elliptical in shape. The hub 12 may be made of plastic, metal, or other suitable material. The hub 12 may include a receptacle for receiving the tubing 13. The tubing 13 may be permanently attached to the hub 12 using a suitable adhesive. In other embodiments, the tubing 13 may be removably attached to the hub 12 using, for example, a luer connection.

The hub 12 may include a controller which allows the fluid delivery device to transition from a first configuration to a second configuration. The first and second configuration may be, for example, a pump reservoir load position and a pump operate position, respectively. While the controller is implemented as a flange in following FIGS. 27-37, it is to be understood that the controller can be implemented in a wide variety of forms, such as, but not limited to, mechanical, electrical, magnetic, or optical forms. For example, without limitation, the hub 12 may include a flange or other mechanical protrusion that interfaces with the pump assembly, or the hub 12 may generate a magnetic field or optical signal that is sensed by a Hull Effect sensor or optical sensor positioned on the pump assembly, respectively. In still another embodiment, a wire in the hub 12 may complete a circuit in the pump assembly.

Figure 27:
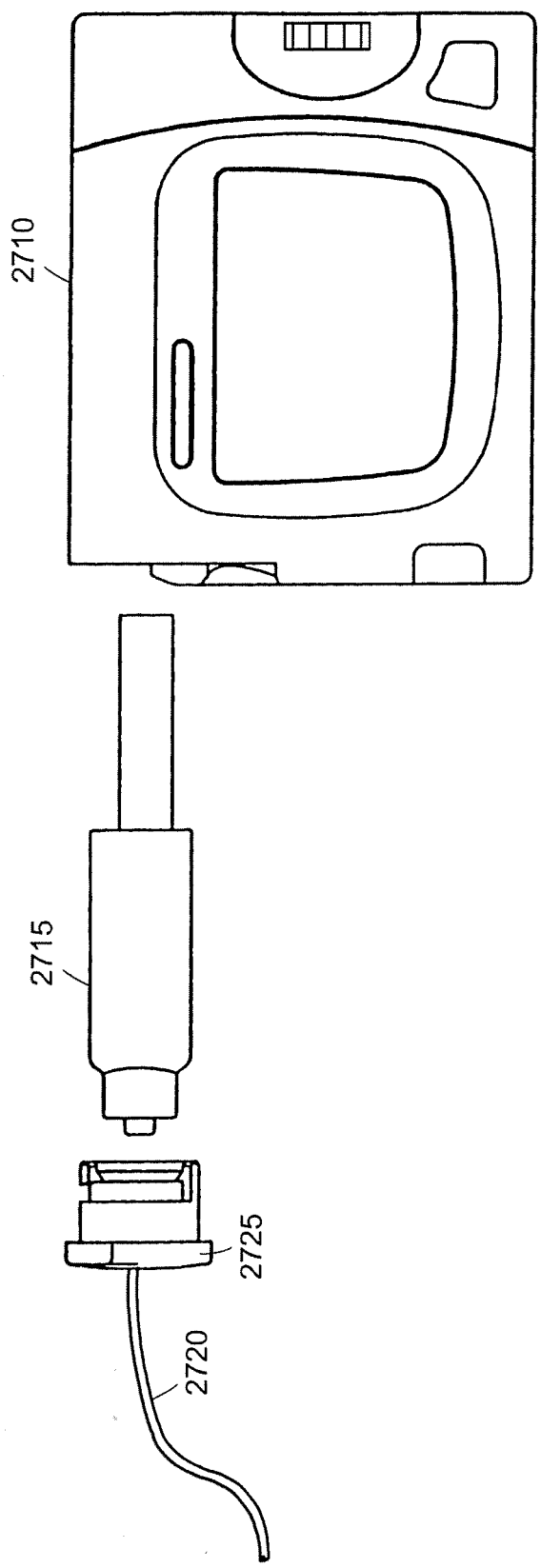
FIG. 27 is a top-level view of a hub and infusion pump, in accordance with one embodiment of the present invention.

FIG. 27 is an overall view of a hub and infusion pump according to one embodiment of the present invention. A pump assembly 2710 contains the components needed to cause a reservoir assembly 2715 to deliver medication to a user. The reservoir assembly 2715 may contain enough medication, such as insulin, for several days for a typical user. A hub 2725 has a coupling to the reservoir assembly, the hub 2725 permanently affixed to a tubing set 2720 for delivery of the fluid to a patient.

Figure 28:
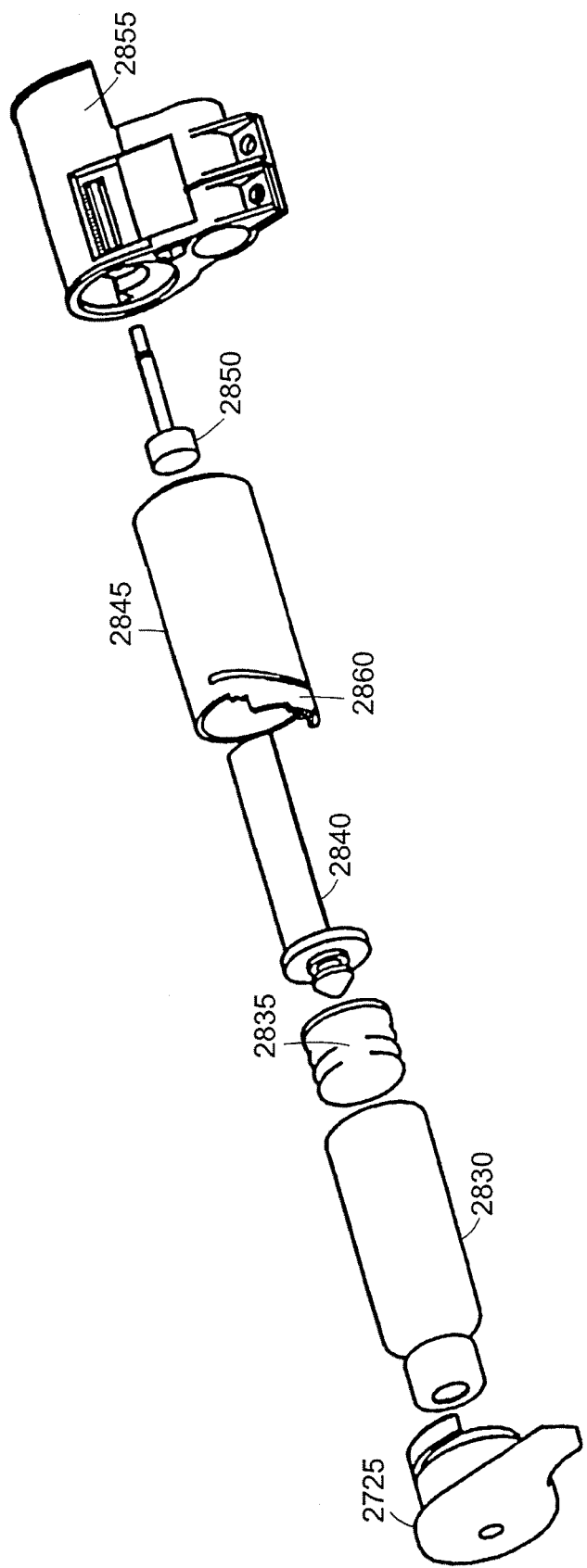
FIG. 28 is an exploded view of a drive mechanism for the infusion pump of FIG. 27.

FIG. 28 shows an exploded view of the drive mechanism of the infusion pump. The reservoir assembly 2715 comprises a reservoir 2830, plunger 2835 and plunger rod 2840. The reservoir 2830 contains the medication for delivery to the user and is of variable interior volume. The interior volume is the liquid capacity of the reservoir. The plunger 2835, inserted into the bottom of the reservoir, causes the volume of the reservoir to change as the plunger is displaced along the longitudinal axis of the reservoir. The plunger rod 2840 is connected to the plunger with the rod's longitudinal axis displaced from and parallel to the longitudinal axis of the reservoir. The plunger rod 2840 is threaded for at least a portion of the rod's length. A cylindrical pump barrel 2845 receives the reservoir assembly 2715. The pump barrel constrains the plunger rod, orienting the rod along the longitudinal axis of the barrel. The pump barrel 2845 is contained in the pump assembly and may contain a locking mechanism, such as a locking tab, to prevent rotation of the pump barrel with respect to the assembly. A gear box 2855 in the pump assembly 2715 includes a drive screw 2850 along with motor and gears to turn the drive screw. The drive screw 2850 is threaded and the screw's longitudinal axis is aligned parallel to and displaced from the longitudinal axis of the pump barrel. The hub 2725 has a coupling to the top of the reservoir.

FIG. 29 shows a pump barrel locking mechanism for an embodiment of the invention. The pump barrel 2845 includes a clearance hole 3072 in one end (shown in FIG. 31) that guides the plunger rod 2840 during insertion of the reservoir assembly 2715 into the barrel 2845. To ensure that the drive screw 2850 does not interfere with the plunger rod 2840 during insertion of the reservoir assembly, the pump barrel 2845 maintains a fixed position relative to the pump assembly 2710. The position of the pump barrel relative to the pump assembly may be maintained, for example, by a locking tab 3060 included in the pump barrel that engages a pump barrel stop 3065 in the pump assembly 10. FIG. 30 is a detailed view of the pump barrel showing the locking tab 3060 and pump barrel stop 3066. Referring back to FIG. 29, the hub 2725 includes a flange 2970 which dislodges the locking tab 3060 from the barrel stop 3065 when the hub 2725 turns, allowing the hub 2725 to rotate the pump barrel 2845.

FIGS. 31 and 32 are views along the longitudinal axis of the pump barrel 2845 showing the relation of the drive screw 2850 to the plunger rod 2840 in a loading position and in an engaged position, respectively. The reservoir assembly 2715 is positioned for loading so that the plunger rod 2840 does not contact the drive screw 2850, as shown in FIG. 31. With the pump barrel 2845 positioned appropriately with respect to the pump assembly 2710, the plunger rod 2840 clearance from the drive screw 2850 is determined by the placement of the clearance hole 3072 in the pump barrel 2845 base, which hole 3072 receives and guides the plunger rod 2840. The clearance hole 3072 may be tapered to ease insertion of the rod 2840. The drive screw 2850 fits in the clearance hole 3072 in the pump barrel 2845. Once the reservoir assembly 2715 is inserted into the pump assembly 2710, the barrel 2845 is rotated by the locking hub 2725, causing the plunger rod 2840 to turn and to engage the drive screw 2850, as shown in FIG. 32. This embodiment advantageously simplifies reservoir loading.

In a specific embodiment of the invention, the plunger rod threads and the drive screw threads are buttress threads. This embodiment advantageously addresses eliminating reaction forces on the plunger rod normal to the direction of the rod's longitudinal axis. Such reaction forces may cause the rod to deflect and skip a thread on the drive screw, resulting in under delivery of medication to the user. Buttress threads eliminate the normal component of the reaction force.

Figure 33:
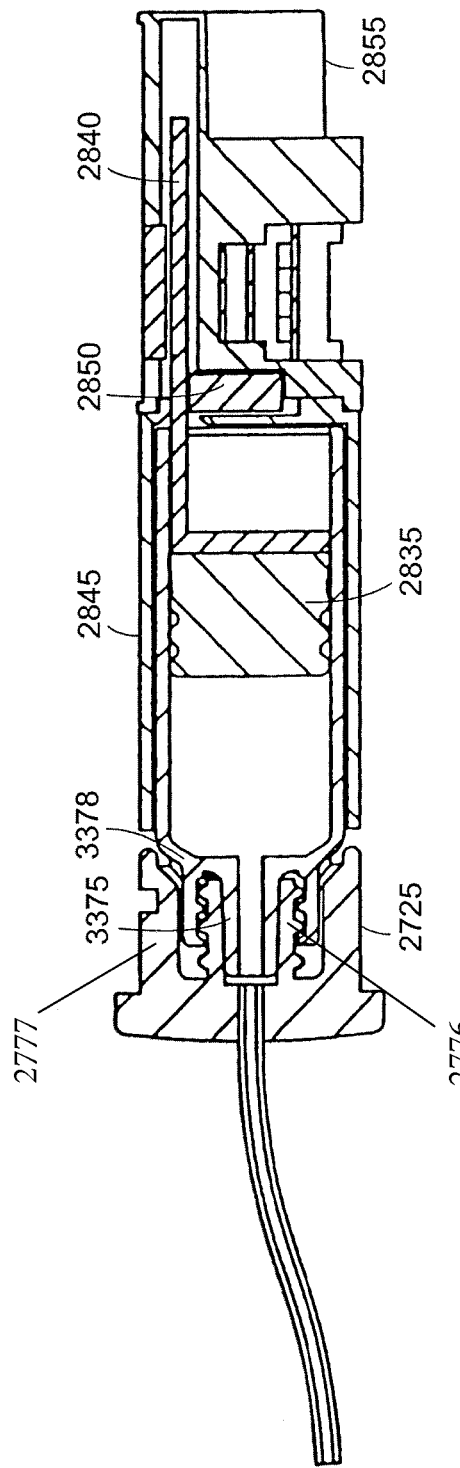
FIG. 33 shows a connection between the locking hub and the reservoir in accordance with one embodiment of the present invention.

In an embodiment of the present invention, the locking hub 2725 may be connected to the reservoir 2830 by a tapered luer connection, as shown in FIG. 33. The reservoir has a male luer taper 3375 integrally molded into the reservoir's top. Surrounding the male luer is an annulus 3378 with an internal female thread. Similarly, the hub 2725 includes the mating female luer and an externally threaded male element 2776 for engaging the internal female thread of the reservoir. The locking hub 2725 also includes a second male element 2777 for engaging with a corresponding element of the pump housing to retain the reservoir 2830 in the barrel 2845 when (a) the hub 2725 is placed in the pump housing so that the hub axis corresponds with the barrel axis and (b) the hub 2725 is rotated.

Figure 34:
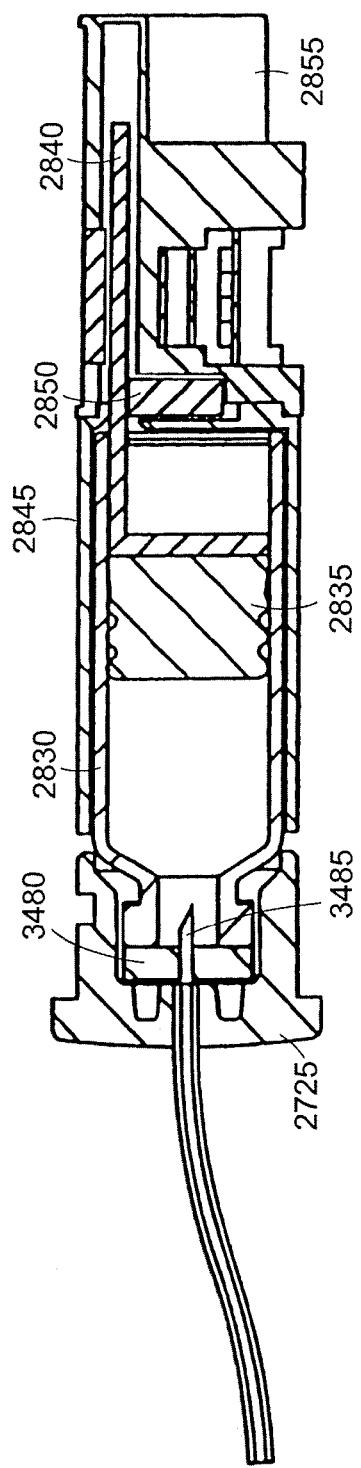
FIG. 34 shows another connection between the locking hub and the reservoir in accordance with one embodiment of the present invention.

In another embodiment of the invention, a needle connection is provided between reservoir 2830 and hub 2725. As shown in FIG. 34, the reservoir includes a rubber septum 3480 that is attached to the reservoir with a crimped metal collar. A needle 3485, integral to the hub, pierces the septum and fluid can then flow from the reservoir to the tubing set.

Figure 35:
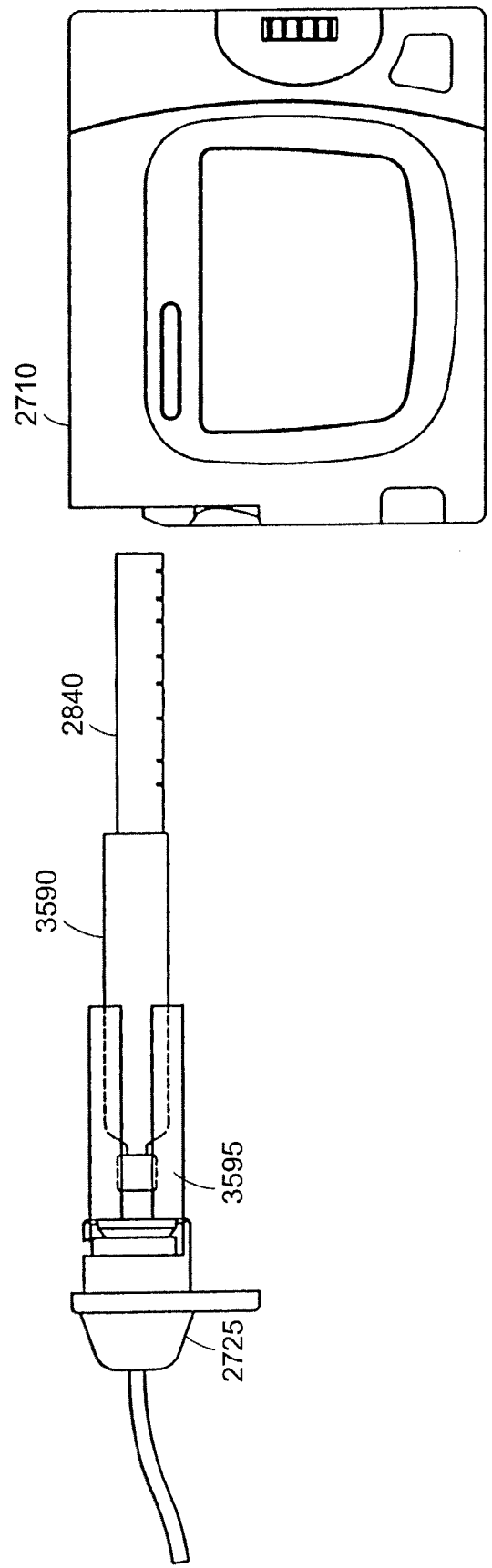
FIG. 35 shows an adapter for using a small diameter reservoir with the pump assembly in accordance with one embodiment of the present invention.
Figure 37:
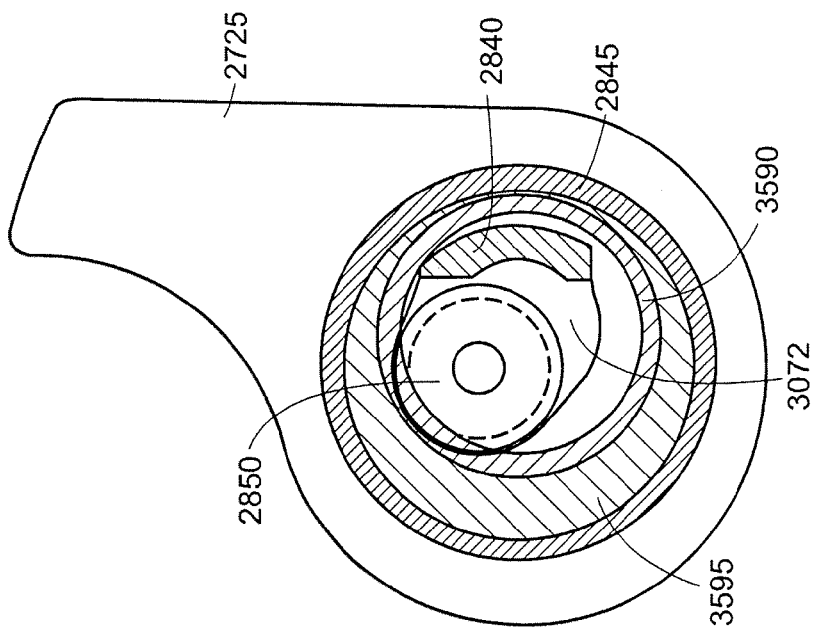
FIG. 37 is an on-axis view of the adapter in FIG. 35 when the pump is in an engaged position.
Figure 36:
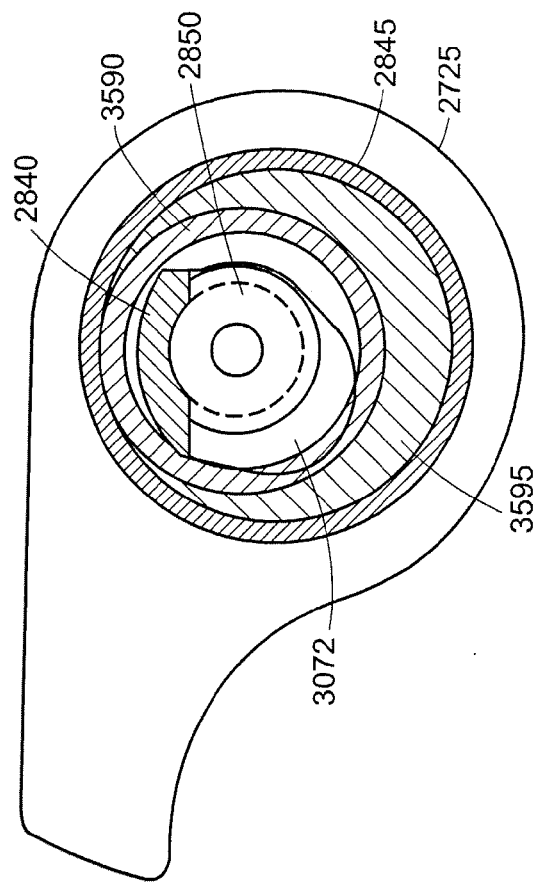
FIG. 36 is an on-axis view of the adapter in FIG. 35 when the pump is in a loading position.

In a further embodiment of the invention, as shown in FIG. 35, an adapter 3595 is provided to permit a reservoir 3590 whose diameter is substantially smaller than the diameter of the pump barrel 2845 to be used with the pump assembly 2710. The adapter 3590 may be a separate component or may be integrated into the locking hub 2725. The adapter 3595 aligns and offsets the reservoir's 3590 axis parallel to the longitudinal axis of the pump barrel so that the plunger rod 2840, when rotated, mates with the drive screw. FIGS. 36 and 37 shows an on-axis view of the small diameter reservoir 3590 when placed in the adapter 3595 in a loading position and in an engaged position, respectively. As will be apparent, the offset provided by the adapter allows the plunger rod 3840, when mated with the plunger 3835 and reservoir 3590, to engage the drive screw 3850 in the same fashion as for the embodiment shown in FIGS. 31 and 32.

Having described various illustrative embodiments of the present invention, some of its advantages and optional features, it will be apparent that such embodiments are presented by way of example only and not by way of limitation. Those skilled in the art could readily devise alterations and improvements on these embodiments, as well as additional embodiments, without departing from the spirit and scope of the invention. All such modifications are within the scope of the invention as claimed.

What is claimed is:

1. A medical device comprising:
   a pump housing including a barrel therein, the barrel having a longitudinal axis and a locking tab in the pump housing; and
   a hub for retaining a replaceable reservoir in the barrel in the pump housing, the hub comprising:
      a first end including a first end face disposed transverse to a hub axis, the first end face including a port disposed along the hub axis, the port having tubing affixed thereto for passage of fluid from the reservoir, the first end face having formed therein a grip to facilitate rotation of the hub about the hub axis;
      a second end including a first male element having an external engagement feature for engaging with a corresponding female element having an internal engagement feature on the reservoir to lock the hub to the reservoir and a second male element for engaging with a corresponding element of the pump housing to retain the reservoir in the barrel when (a) the hub is placed in the pump housing so that the hub axis corresponds with the barrel axis and (b) the hub is rotated; and
      a controller including a mechanical protrusion that is a flange and is adapted to dislodge the locking tab on the barrel in the pump housing to transition a fluid delivery device within the pump housing from a reservoir load position to an operate position upon a rotation of the hub about the hub axis.

2. A hub according to claim 1 wherein the grip is a cam.

3. The hub according to claim 1, additionally comprising a female luer connection disposed within the first male element for engaging a corresponding male luer connection of the reservoir.

4. The hub according to claim 1, wherein the controller allows the barrel to rotate to bring rod threads of a plunger rod disposed within the barrel into and out of mechanical engagement with a drive screw of the fluid delivery device.

5. A medical device comprising:
   a pump housing including a barrel therein, the barrel having a longitudinal axis and a locking tab in the pump housing; and
   a hub for retaining a replaceable reservoir in the barrel in the pump housing, the hub comprising:
      a first end including a first end face disposed transverse to a hub axis, the first end face including a port disposed along the hub axis, the port adapted to have tubing attached thereto for passage of fluid from the reservoir, the first end face having formed therein a grip to facilitate rotation of the hub about the hub axis;
      a second end including a first male element having an external engagement feature for engaging with a corresponding female element having an internal engagement feature on the reservoir to lock the hub to the reservoir and a second male element for engaging with a corresponding element of the pump housing to retain the reservoir in the barrel when (a) the hub is placed in the pump housing so that the hub axis corresponds with the barrel axis and (b) the hub is rotated; and
      a controller including a mechanical protrusion that is a flange and is adapted to dislodge the locking tab on the barrel in the pump housing to transition a fluid delivery device within the pump housing from a reservoir load position to an operate position upon a rotation of the hub about the hub axis.

6. The hub according to claim 5, wherein the port is adapted to have the tubing removably attached thereto.

7. The hub according to claim 6, wherein the port includes a luer connection for attaching the tubing thereto.

8. The hub according to claim 5, wherein the grip is a cam.

9. The hub according to claim 5, additionally comprising a female luer connection disposed within the first male element for engaging a corresponding male luer connection of the reservoir.

10. The hub according to claim 5, wherein the controller allows the barrel to rotate to bring rod threads of a plunger rod disposed within the barrel into and out of mechanical engagement with a drive screw of the fluid delivery device.

\* \* \* \* \*